(12) United States Patent
Yaqoob et al.

(10) Patent No.: US 9,557,549 B2
(45) Date of Patent: Jan. 31, 2017

(54) SYSTEMS AND METHODS FOR SELF-REFERENCED QUANTITATIVE PHASE MICROSCOPY

(71) Applicant: Massachusetts Institute of Technology, Cambridge, MA (US)

(72) Inventors: Zahid Yaqoob, Cambridge, MA (US); Niyom Lue, Nahant, MA (US); Timothy Robert Hillman, New York, NY (US)

(73) Assignee: Massachusetts Institute of Technology, Cambridge, MA (US)

( * ) Notice: Subject to any disclaimer, the term of this patent is extended or adjusted under 35 U.S.C. 154(b) by 322 days.

(21) Appl. No.: 14/363,686

(22) PCT Filed: Dec. 10, 2012

(86) PCT No.: PCT/US2012/068814
§ 371 (c)(1),
(2) Date: Jun. 6, 2014

(87) PCT Pub. No.: WO2013/086527
PCT Pub. Date: Jun. 13, 2013

(65) Prior Publication Data
US 2014/0375792 A1   Dec. 25, 2014

Related U.S. Application Data

(60) Provisional application No. 61/568,956, filed on Dec. 9, 2011.

(51) Int. Cl.
*G02B 21/00* (2006.01)
*G02B 21/14* (2006.01)
(Continued)

(52) U.S. Cl.
CPC ............ *G02B 21/0056* (2013.01); *G01J 9/02* (2013.01); *G01N 21/453* (2013.01); *G02B 21/14* (2013.01); *G02B 21/365* (2013.01)

(58) Field of Classification Search
CPC ..... G01B 9/02; G01B 11/2441; G01B 21/365; G01B 21/367; G01B 21/002; G01J 11/00; G01J 9/02; G01J 9/0246; G01N 21/45; G01N 21/4795; G01N 21/6458; A61B 5/0066; A61B 3/102; H04N 7/18; G02B 21/002
See application file for complete search history.

(56) References Cited

U.S. PATENT DOCUMENTS 4,596,145 A   6/1986 Smith et al.
4,694,434 A   9/1987 von Ramm et al.
(Continued)

FOREIGN PATENT DOCUMENTS

CN   1156101C C   6/2004
JP   07318806   12/1995
(Continued)

OTHER PUBLICATIONS

Arnison et al., "Using the Hilbert Transform for 3D Visualization of Differential Interface Contrast Microscope Images", Journal of Microscopy, vol. 199, Pt. 1, pp. 79-84, Jul. 2000.
(Continued)

*Primary Examiner* — Sath V Perungavoor
*Assistant Examiner* — Howard D Brown, Jr.
(74) *Attorney, Agent, or Firm* — McCarter & English, LLP

(57) ABSTRACT

Systems and methods of self-referenced quantitative phase microscopy (SrQPM). The SrQPM systems and methods provide single-shot, full-field imaging capability for increased imaging speed, and near-common-path geometry
(Continued)

Self-referenced quantitative phase microscope (SrQPM)

for increased phase stability, allowing the study of internal structures of biological cells, live cell dynamics, and the like.

73 Claims, 15 Drawing Sheets

(51) Int. Cl.
*G02B 21/36* (2006.01)
*G01N 21/45* (2006.01)
*G01J 9/02* (2006.01)
*G01B 9/02* (2006.01)

(56) References Cited

U.S. PATENT DOCUMENTS

| | | | |
|---|---|---|---|
| 5,194,918 A | 3/1993 | Kino et al. | |
| 5,453,835 A | 9/1995 | Ward et al. | |
| 5,747,810 A | 5/1998 | Schotland | |
| 6,456,380 B1 | 9/2002 | Naganuma | |
| 6,549,801 B1 | 4/2003 | Chen et al. | |
| 6,611,339 B1 | 8/2003 | Yang et al. | |
| 6,665,456 B2 | 12/2003 | Dave et al. | |
| 6,868,347 B2 | 3/2005 | Li et al. | |
| 8,525,998 B2 | 9/2013 | Yaqoob et al. | |
| 2002/0097402 A1 | 7/2002 | Manning | |
| 2002/0102011 A1* | 8/2002 | Bacus | G06F 19/20 382/128 |
| 2003/0081220 A1 | 5/2003 | Ostrovsky et al. | |
| 2005/0057756 A1* | 3/2005 | Fang-Yen | G01B 9/02072 356/497 |
| 2005/0105097 A1* | 5/2005 | Fang-Yen | A61B 5/1455 356/497 |
| 2006/0192969 A1 | 8/2006 | Marks et al. | |
| 2006/0209370 A1* | 9/2006 | Coppola | G03H 1/0866 359/9 |
| 2006/0291712 A1 | 12/2006 | Popescu et al. | |
| 2008/0259345 A1* | 10/2008 | Fukutake | G02B 21/18 356/450 |
| 2009/0059360 A1* | 3/2009 | Evans | G01N 21/6458 359/370 |
| 2009/0125242 A1* | 5/2009 | Choi | G01N 21/45 702/19 |
| 2010/0054415 A1* | 3/2010 | Olivo | G01N 23/04 378/85 |
| 2011/0032536 A1 | 2/2011 | Kuriyama et al. | |
| 2013/0128042 A1* | 5/2013 | Bridge | H04N 5/232 348/143 |
| 2013/0286400 A1* | 10/2013 | Kim | G01B 9/04 356/450 |

FOREIGN PATENT DOCUMENTS

| | | |
|---|---|---|
| JP | 2002526815 A | 8/2002 |
| WO | 200020929 A1 | 4/2000 |

OTHER PUBLICATIONS

Belvaux et al., "Visualization of Phase Objects by Hilbert Transformation", Nouvelle Revue d'Optique Appliquée, France, vol. 2, No. 3, pp. 149-162, 1971.

Ikeda et al., "Hilbert Phase Microscopy of Investigating Fast Dynamics in Transparent Systems", Optics Letters, vol. 30, No. 10, pp. 1165-1167, 2005.

Kniffen et al., "Bispectral Magnitude and Phase Recovery Using a Wide Bandwidth Acousto-Optic Processor", Applied Optics, vol. 33, No. 8, Mar. 1992.

Lowenthal et al., "Observation of Phase Objects by Optically Processed Hilbert Transform", Applied Physics Letters, vol. 11, No. 2, pp. 49-51, 1967.

Massatsch, et al., "Time-Domain Optical Coherence Tomography with Digital Holographic Microscopy", Applied Optics, vol. 44, No. 10, pp. 1806-1812, Apr. 2005.

Popescu et al., "Erythrocyte Structure and Dynamics Quantified by Hilbert Phase Microscopy", Journal of Biomedical Optics, vol. 10, No. 6, pp. 060503-1-060503-3, 2005.

Popescu et al., "Imaging Red Blood Cell Dynamics By Quantitative Phase Microscopy", Blood Cells, Molecules and Diseases 41, pp. 10-16, 2008.

Watanabe et al., "Time-Gated Full-Field Optical Coherence Tomography Using Optical Hilbert Transformation", Biotphotonics, pp. 10-11, 2004.

Yamauchi, et al., "Low-Coherent Quantitative Phase Microscope for Nanometer-Scale Measurement of Living Cells Morphology", Optics Express, vol. 16, No. 16, pp. 12227-12238, 2008.

Choi et al., "Full-Field and Single-Shot Quantitative Phase Microscopy Using Dynamic Speckle Illumination", Optics Letters, vol. 36, No. 13, pp. 2465-2467, Jul. 2011.

International Search Report for PCT/US12/68814 mailed on Apr. 12, 2013.

* cited by examiner

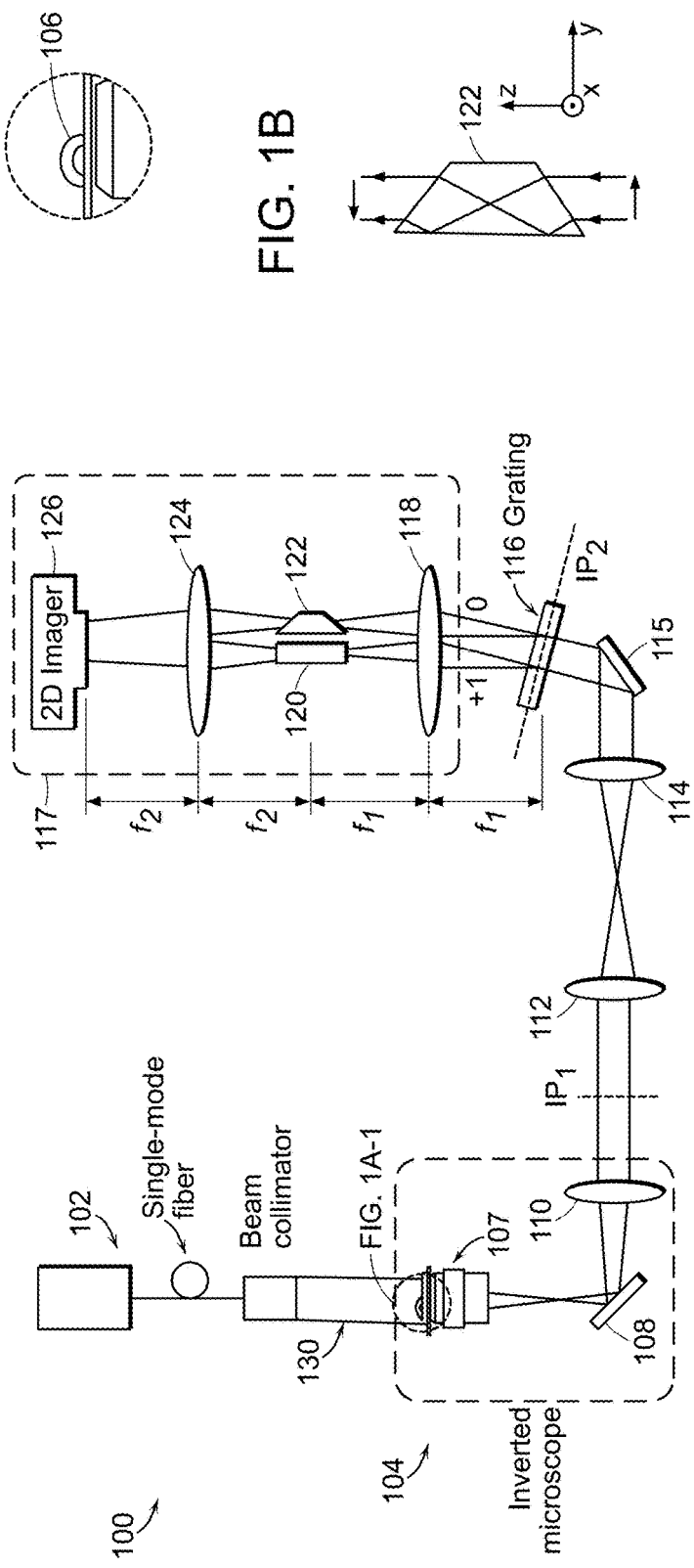
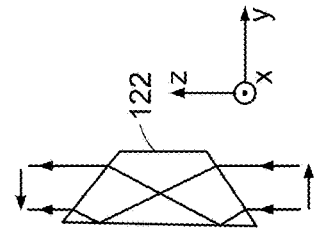
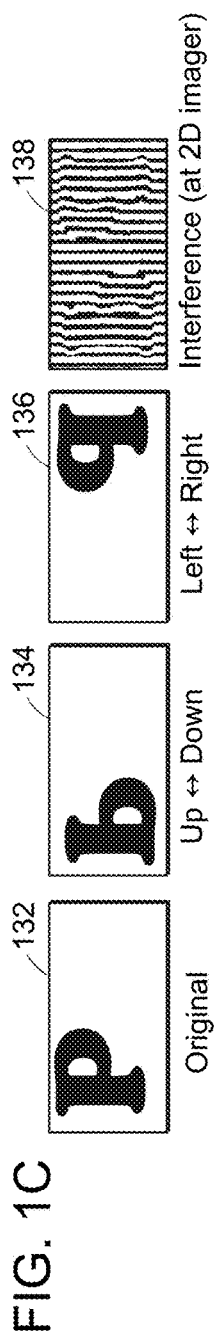

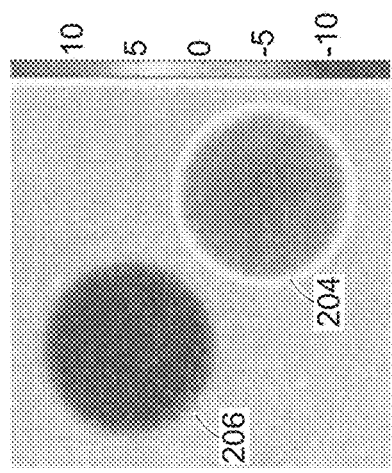
FIG. 2A
FIG. 2B
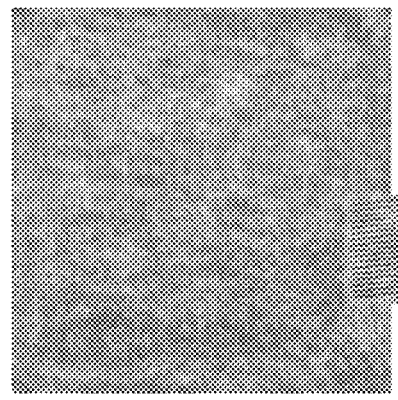
FIG. 2C
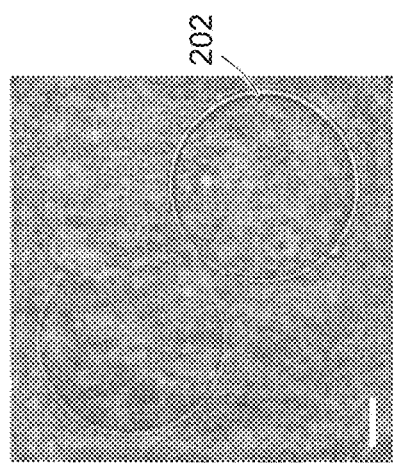
FIG. 2D
FIG. 2E
FIG. 2E
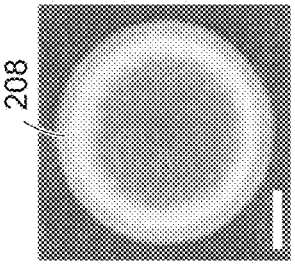
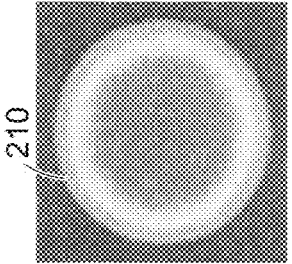
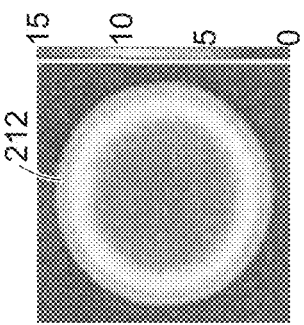
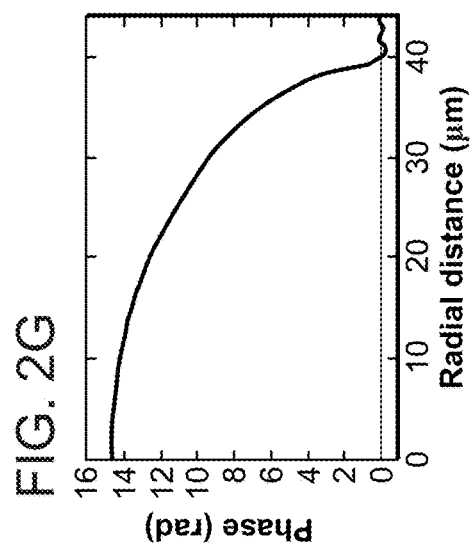
FIG. 2G

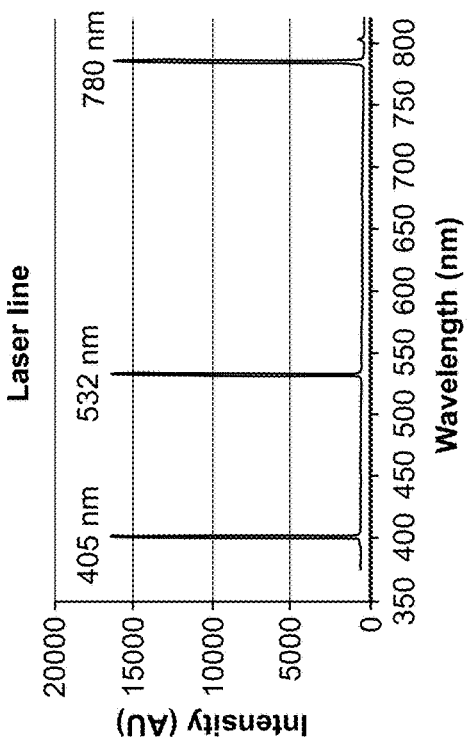
FIG. 5B
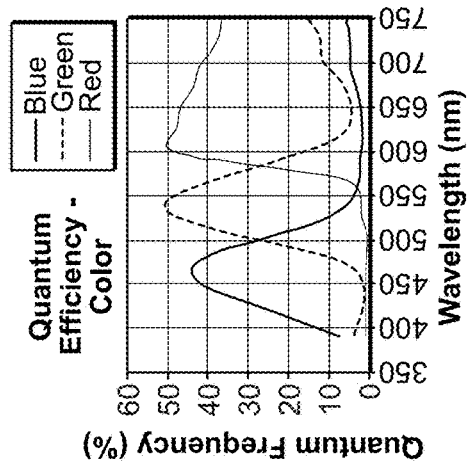
FIG. 5C
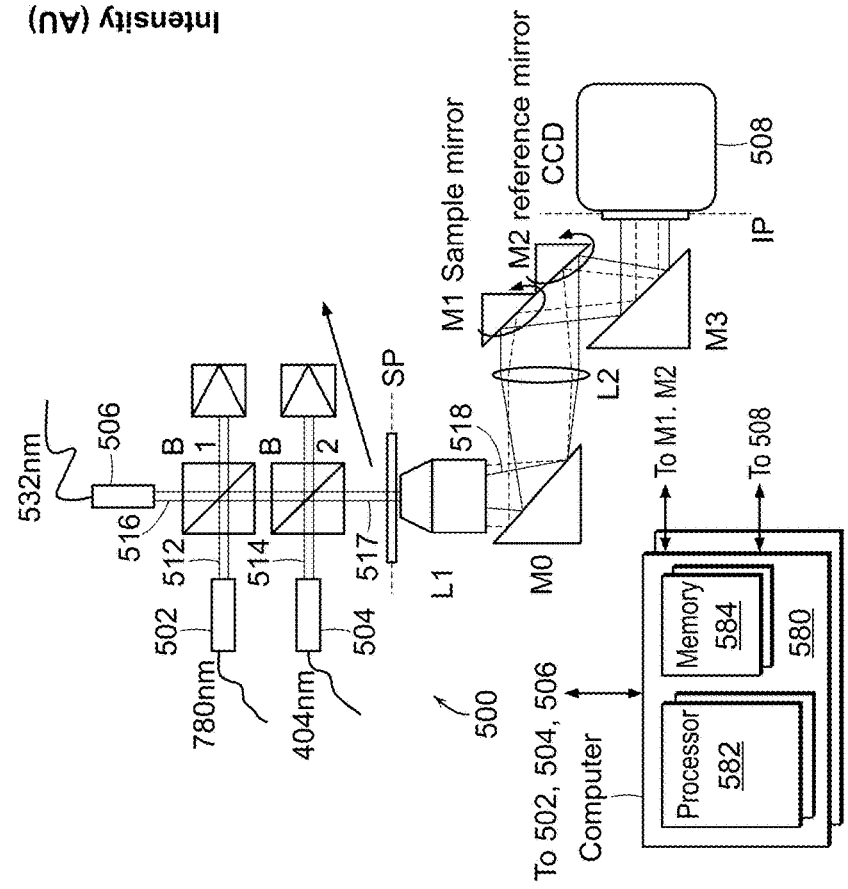
FIG. 5A   Demonstrated multi-spectral SrQPM

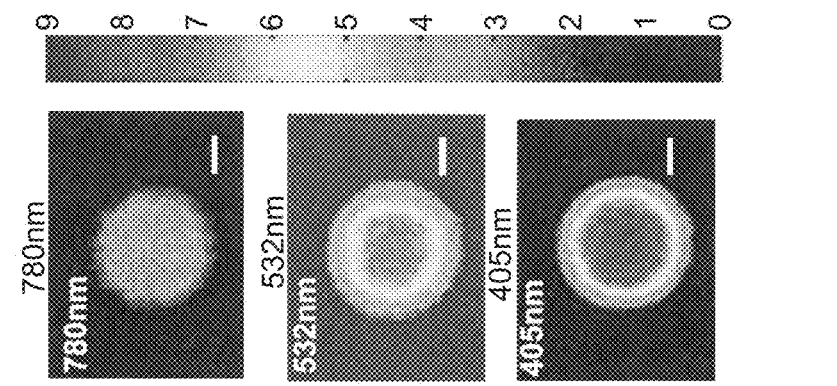
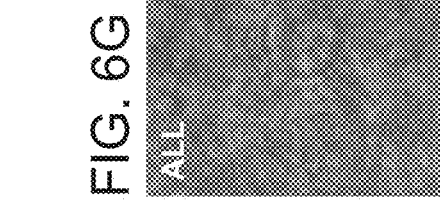
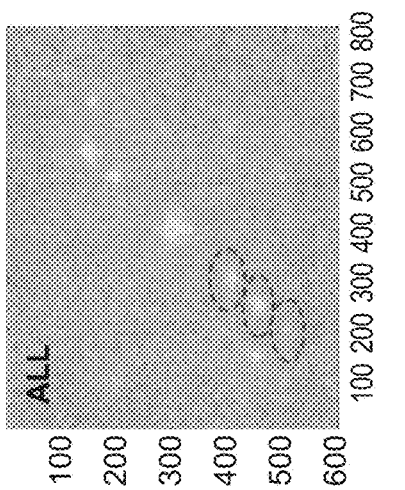
FIG. 6A  FIG. 6B  FIG. 6C
FIG. 6D  FIG. 6E  FIG. 6F
FIG. 6G  FIG. 6H
FIG. 6I  FIG. 6J  FIG. 6K

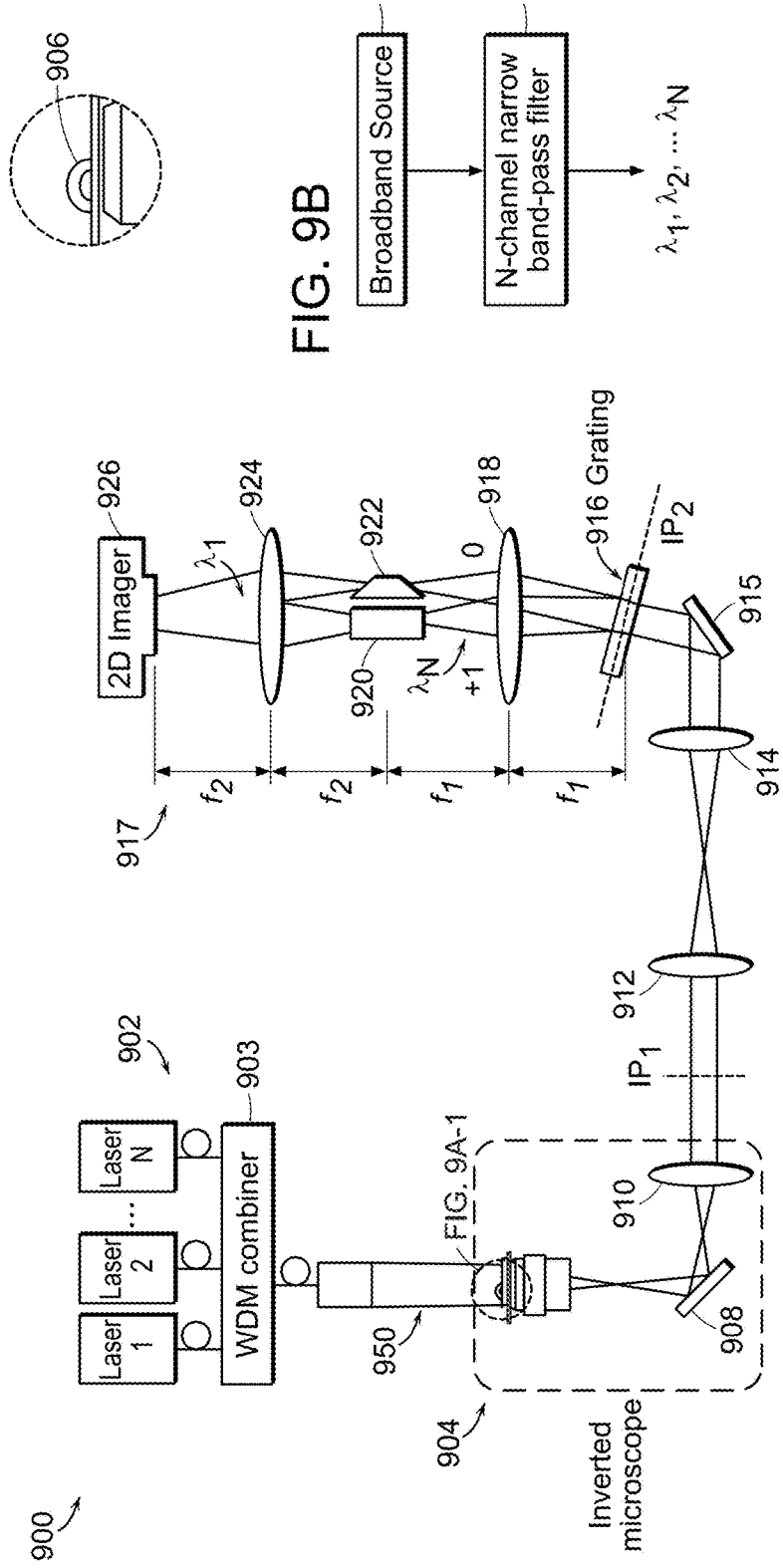

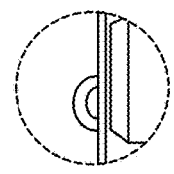
FIG. 11B-1
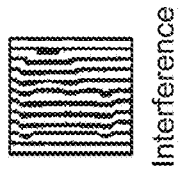
FIG. 11C
Interference
FIG. 11B
Simpler multi-spectral SrQPM design
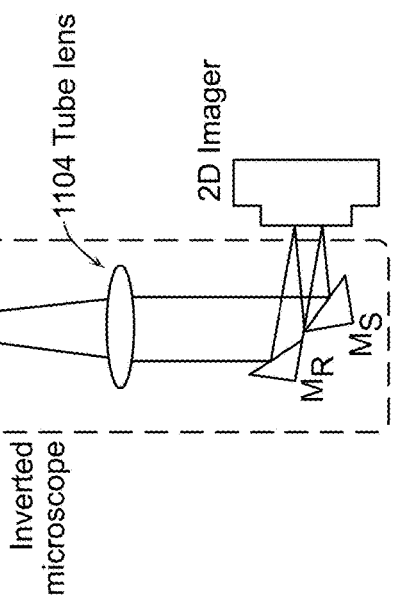
Multi-channel light source
FIG. 11B-1
Sample 1102
1104 Tube lens
2D Imager
$M_R$  $M_S$
Inverted microscope
FIG. 11A
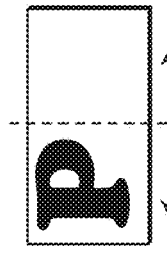
Right half of FOV with empty region
Left half of FOV with sample

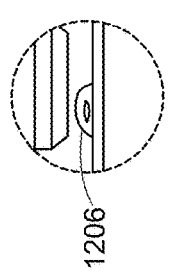
FIG. 12-1
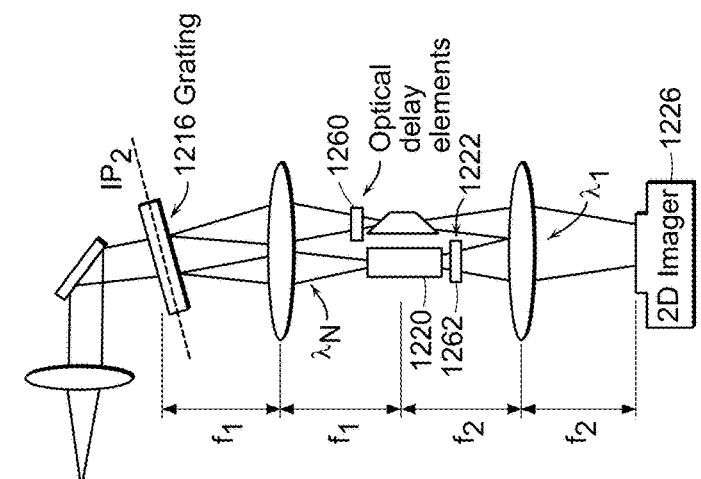
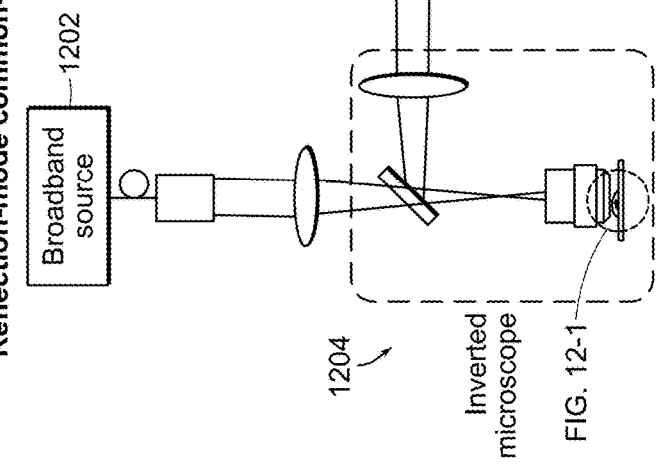
FIG. 12

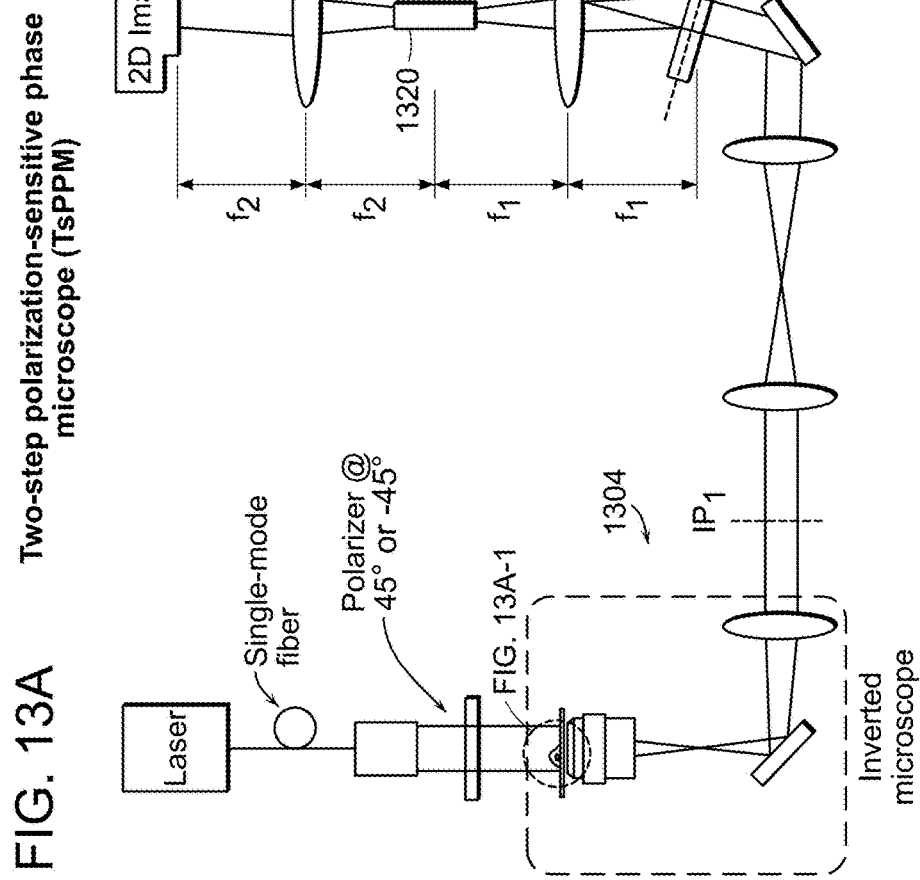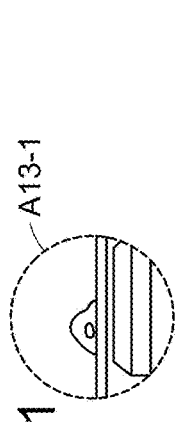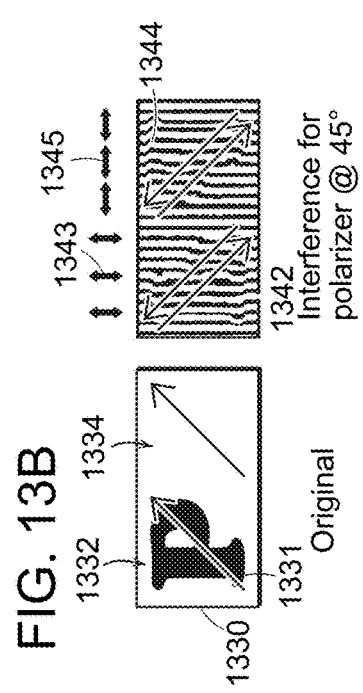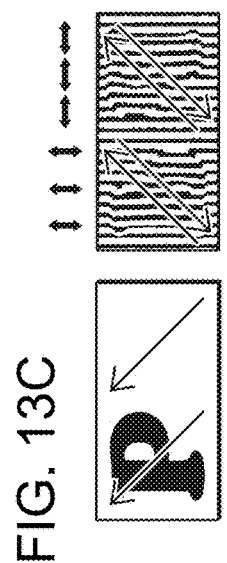

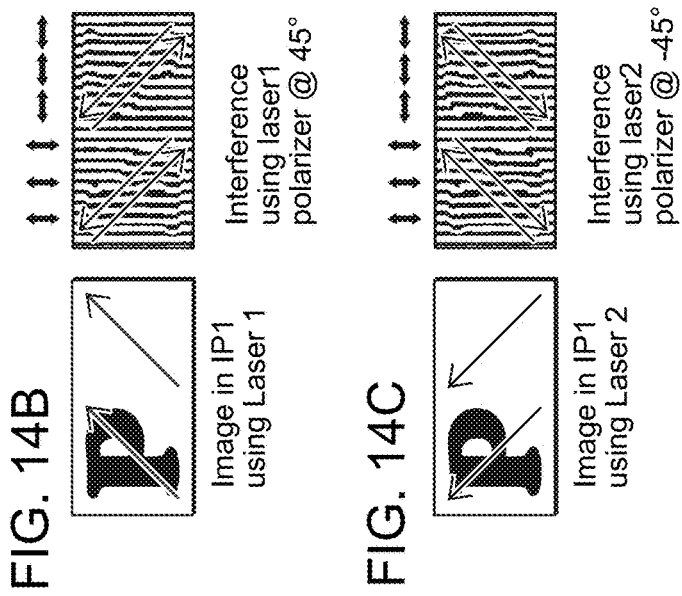
FIG. 14A-1
FIG. 14B  Image in IP1 using Laser 1
FIG. 14C  Image in IP1 using Laser 2
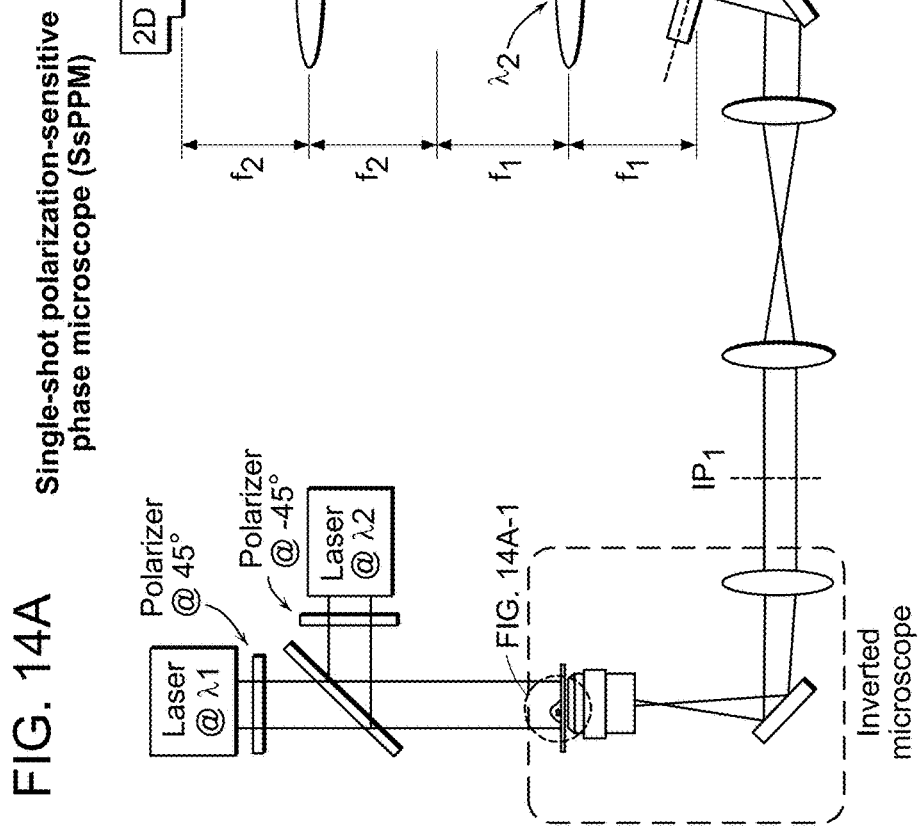
FIG. 14A  Single-shot polarization-sensitive phase microscope (SsPPM)

SYSTEMS AND METHODS FOR SELF-REFERENCED QUANTITATIVE PHASE MICROSCOPY

CROSS REFERENCE TO RELATED APPLICATION

This application is a 35 U.S.C. §371 national stage filing of International Application No. PCT/US2012/068814, filed on Dec. 10, 2012, which claims priority to, and the benefit of, U.S. Provisional Application No. 61/568,956, filed on Dec. 9, 2011, the entire contents of the above applications are being incorporated herein by reference.

STATEMENT REGARDING FEDERALLY SPONSORED RESEARCH OR DEVELOPMENT

This invention was made with Government support under Grant No. RR002594 awarded by the National Institutes of Health and under Grant No. DBI0754339 awarded by the National Science Foundation. The Government has certain rights in the invention.

BACKGROUND OF THE INVENTION

Systems and methods of quantitative phase microscopy (QPM) are known that employ digital holography for studying the internal structures of biological cells without requiring the use of exogenous staining. Systems and methods of diffraction phase microscopy (DPM) based on off-axis point diffraction interferometry that allow quantitative phase imaging through a combination of single-shot imaging and a near-common-path geometry are also known.

In such known systems and methods of DPM, a technique can be employed in which an off-axis hologram image is recorded between two optical waves that are both derived from light transmitted through a sample. The two optical waves are the zero-th and first order beams that are generated when the transmitted light is incident upon an optical grating, which is the point where the optical wave paths diverge. The optical waves recombine at a detection plane after the zero-th order beam has passed through a Fourier-plane pinhole spatial filter, allowing the zero-th order beam to perform the function of a plane reference beam in the imaging plane. This technique has been characterized as having sub-nanometer path-length stability and millisecond-scale acquisition time.

Some known QPM systems employ an in-line point-diffraction-interferometry configuration that provides improved measurement resolution. In such a configuration, phase stepping (which is generally required for a non-off-axis geometry) is achieved by translating a transmission grating in a direction orthogonal to the optical axis. A variation of such a configuration that employs a pair of cube beam splitters (instead of transmission gratings), and several polarization-transforming optical elements, can simultaneously acquire two sample hologram images, phase-shifted with respect to each other, on different regions of a CCD detector.

In addition, systems and methods of QPM are known that employ a Zernike phase contrast approach, as opposed to holographic interferometry, to provide increased lateral resolution and reduced coherent noise. In such an approach, an illumination pattern consists of a series of discrete points evenly spaced around a circle, allowing phase stepping to be achieved by rotating a phase plate having structures etched onto a similarly sized circle. Such structures can help to mitigate halo and shade-off artifacts.

DPM is known to employ a Zernike phase contrast approach. This technique is referred to herein as instantaneous spatial light interference microscopy (iSLIM) in which a reference beam is passed through an annular aperture, and an optical grating and an amplitude mask are used to introduce a phase ramp between un-diffracted and diffracted components of an object wave, allowing an off-axis interferogram to be recorded between the object wave components. In this way, the stability of DPM can be combined with white-light illumination, which can diminish coherent speckle effects and enable spectroscopic imaging.

One drawback of the known methods of QPM/DPM that require a reference beam to be passed through a Fourier-plane pinhole spatial filter or an annular aperture as in iSLIM, is that they can create an alignment constraint that can increase the complexity of the systems, which is particularly problematic for non-specialists in the fields of QPM/DPM. Further, the size of the pinhole in the Fourier-plane pinhole spatial filter, or the size of the annular aperture, must typically be optimized with respect to the system optics, further contributing to the complexity of the systems and methods.

Some known systems and methods are known employ a self-referenced QPM technique, in which a transmitted sample wave is propagated through a Michelson interferometer that performs an image inversion after a double pass using an additional objective lens in one of its arms. In one known implementation of the self-referenced QPM technique, a phase-shifting procedure can be used to recover a sample-wave phase profile, while scanning a minor in the object arm to achieve an extended depth-of-field. To reduce temporal phase noise introduced between successive phase-stepped images, another known implementation of the self-referenced QPM technique is provided that uses Hilbert phase microscopy to determine the sample-wave phase profile. However, both known implementations of the self-referenced QPM technique described above employ separate sample and reference arms, making them susceptible to spatial phase noise.

Systems and methods of QPM can be used to provide the anisotropy of a sample under observation. The drawbacks of the known self-referenced QPM systems above include i) a system configuration that is not common-path, which can lead to spatial phase instability, and ii) requiring four serial measurements, which may be time consuming, requires sample to be stationary, and can introduce temporal phase noise.

It would therefore be desirable to have improved systems and methods of self-referenced quantitative phase microscopy (SrQPM) that avoid at least some of the drawbacks of the known systems and methods of QPM/DPM described above.

SUMMARY OF THE INVENTION

The present application relates in general to systems and methods of quantitative phase microscopy, and more particularly to systems and methods of self-referenced quantitative phase microscopy (SrQPM) and multi-spectral SrQPM that have single-shot, full-field imaging capability for increased imaging speed, and near-common-path geometry for increased phase stability, allowing the study of internal structures of biological cells, live cell dynamics, and the like.

Systems and methods of quantitative phase microscopy provide a two-dimensional optical-path-length (OPL) profile of a sample that is usually wavelength-specific. The knowledge of wavelength-dependent OPL (or optical dispersion) in biological samples can be useful to understand the underlying chemical information, to advance mathematical modeling of light-matter interaction, and to correct undesired optical distortion to improve image resolution. Systems and methods can be employed to make wavelength-dependent quantitative phase measurements for determining the hemoglobin concentrations in red blood cells, or other cellular characteristics for example. Some embodiments can eliminate the need for various band pass filters that can be used together with a white light source for serial selection of wavelengths for spectroscopic phase measurements. Further, prior methods require the sample to be static, which is not appropriate for dynamic measurements or for the case when the sample (e.g., a cell) is in motion.

In a preferred embodiment, a quantitative phase system is disclosed that can form a quantitative phase image through the interference of a sample wave with a rotated version of itself. The system includes a pair of optical elements, such as dove prisms, with different orientations, to effect the relative transformation of light between sample and reference beams. Some SrQPM systems described herein eliminate the requirement of conventional diffraction phase microscope (DPM) systems in which the sample wave illumination is transmitted through a pinhole spatial filter in order to generate a plane reference wave in the imaging plane for interference. SrQPM systems described herein effectively relax an alignment constraint associated with conventional DPM, rendering the systems more accessible to non-specialists, and more amenable to long-term measurements over several sample cycles.

In preferred embodiments of SrQPM systems described herein, because the sample wave interferes with a 180° rotated version of itself, a first region such as half of the object field-of-view is used for the sample, while the other "empty" half or bypass region of the field-of-view that is used for self-referencing. Provided that approximately one-half of the object field-of-view is optically flat, the SrQPM system permits a quantitative phase image of the sample to be recovered. This provides a "single beam" method where a sample is placed in a sampling region and a first portion of the beam illuminates the sample and a second portion of the sampling region that does not illuminate the sample (i.e. the bypass region) is used as a reference. The SrQPM system provides a number of advantages, including its near-common-path geometry, and its single-shot wide-field imaging capability. Such advantages translate to dynamic phase measurements with sub-nanometer measurement sensitivity and millisecond imaging speed.

In an exemplary aspect, the SrQPM system includes a light source, an inverted microscope including an objective lens, a first mirror, and a first lens, a plurality of magnification lenses, a second mirror, an optical separating element such as a diffraction grating, an imaging system including a plurality of lenses and a pair of prisms, and a detector. In another exemplary aspect, the light source may be a highly spatially coherent light source, the imaging system may be a 4f imaging system, the pair of prisms may be a pair of dove prisms, and the detector can be a high-speed CMOS camera.

In accordance with an exemplary mode of operation, light from a single-mode fiber of the light source is collimated and incident upon a sample, which can occupy one-half or less of the field-of-view of the objective lens. The light is collected by the objective lens, reflected off of the first mirror, and passed through the first lens to a first image plane. The light is passed through the first image plane, magnified by the magnification lenses, reflected off of the second mirror, and incident upon the diffraction grating in a conjugate image plane IP2. A zero-th order beam (0) and a first order beam (+1) (or higher order component) are generated by the diffraction grating, and subsequently passed through one of the lenses in the imaging system. The first order beam (+1) and the zero-th order beam (0) are also passed through the pair of dove prisms, and ultimately passed through another one of the lenses in the imaging system to be recombined and imaged onto a detection plane of the detector to obtain interference image data.

In another aspect, a multi-spectral SrQPM system is disclosed. The disclosed multi-spectral SrQPM system employs red, green, and blue lasers, and color filters in a color camera to separate multi-spectral interference fringes. The multi-spectral SrQPM system can acquire single-shot, relatively full-field (e.g., half-field), multi-color interferograms that can be post-processed to determine wavelength-dependent optical phase delay information of the sample. Alternatively, a broadband source with a plurality of narrow band-pass filters can be used to provide a plurality of colors. A white light source, such as a halogen lamp, can be used with an annular ring for this purpose to reduce speckle.

In an exemplary aspect, the multi-spectral SrQPM system includes a plurality of light sources, a plurality of beam splitters, a first lens, a tube lens, a plurality of mirrors, and a detector. In another exemplary aspect, the light sources may be implemented as near-UV, green, and near-IR diode lasers.

In accordance with an exemplary mode of operation, light from the near-UV, green, and near-IR diode lasers, for example, are collimated and combined into a single beam by the beam splitters, before reaching a sample plane or region. Having reached the sample plane, the single beam is collected as multi-spectral light by the tube lens. The multi-spectral light is then redirected by the plurality of mirrors to the detector. Specifically, a sample mirror M1 redirects a sample beam that bypasses the sample to the detector, and a reference mirror redirects a reference beam to the detector. The field-of-view is therefore effectively divided in two, with one portion, such as one half of the field-of-view corresponding to the reference beam, traveling through the background medium alone, and the second portion, or the other half of the field-of-view corresponding to the sample beam, traveling through the sample. By having the sample beam and the reference beam impinge upon different mirrors, namely, the sample mirror and the reference mirror, which can be tilted independently, the sample beam and the reference beam can be brought to interfere with each other at an image plane of the detector. Further, by appropriately tilting the sample and reference mirrors, the sample beam and the reference beam can be made to travel to the image plane of the detector substantially in parallel along a common optical path. A control system can be used to control positioning of system elements. Note that preferred embodiments can operate in a reflection mode.

Other features, functions, and aspects of the invention will be evident from the Drawings and/or the Detailed Description of the Invention that follow.

BRIEF DESCRIPTION OF THE DRAWINGS

The invention will be more fully understood with reference to the following Detailed Description in conjunction with the drawings of which:

FIGS. 1A and 1A-1 include a diagram of an illustrative embodiment of an exemplary self-referenced quantitative phase microscopy (SrQPM) system to image a sample, according to the present application;

FIG. 1B is a ray-tracing diagram illustrating how a dove prism included in the SrQPM system of FIG. 1A can operate to horizontally flip an image formed by a zero-th order beam (0) relative to an original image of a sample;

FIG. 1C includes diagrams illustrating an exemplary original image of a sample, an exemplary image of the sample vertically flipped relative to the original image of the sample (e.g., by a first dove prism), an exemplary image of the sample horizontally flipped relative to the original image of the sample (e.g., by a second dove prism with a different orientation), and an exemplary hologram interference image when the vertically and horizontally flipped waves meet each other in the detector plane;

FIGS. 2A-2B illustrate a single-shot hologram image recorded in the presence of a sample, and a hologram image recorded in the absence of the sample;

FIG. 2C illustrates recovery of twin, phase-conjugate reconstructions of the hologram interference images of the sample in FIG. 2A based on the phase difference between first and zero-th order wave fields, following removal of the background phase ramp using the hologram image of FIG. 2B and two-dimensional phase unwrapping;

FIG. 2D-2E illustrate cropped phase-reconstructed images of the sample corresponding to the holographic interference images of FIGS. 2A-2B, after applying low-order aberration correction and image registration;

FIG. 2F illustrates a combined, mean phase profile based on the phase-reconstructions of FIGS. 2D-2E;

FIG. 2G illustrates radial phase profiles for the phase images that correspond to the holographic reconstructions of the sample of FIGS. 2A-2B, illustrating near-perfect matching between the radial phase profiles;

FIG. 5A is a schematic diagram of an illustrative embodiment of an exemplary multi-spectral, self-referenced quantitative phase microscopy (SrQPM) system, according to the present application;

FIG. 5B is a diagram illustrating measured spectra for multi-color diode lasers included in the multi-spectral SrQPM system of FIG. 5A;

FIG. 5C is a diagram illustrating an exemplary RGB spectral response of a detector included in the multi-spectral SrQPM system of FIG. 5A;

FIGS. 6A-6C illustrate interferogram images of a polystyrene bead when each of a plurality of multi-color diode lasers included in the multi-spectral SrQPM system of FIG. 5A is turned on one at a time;

FIGS. 6D-6F illustrate fast Fourier transform (FFT) images corresponding to the respective interferogram images of FIGS. 6A-6C;

FIGS. 6G-6H illustrate a single-shot three-color processing interferogram image of the bead of FIGS. 6A-6C when all three of the diode lasers included in the multi-spectral SrQPM system of FIG. 5A are turned on at the same time, and a FFT image corresponding to the interferogram image;

FIGS. 6I-6K illustrate simultaneously acquired quantitative phase images of the bead of FIGS. 6A-6C at three diode laser wavelengths;

FIGS. 9A-9C are diagrams illustrating an alternative embodiment of a multi-spectral SrQPM system, according to the present application;

FIGS. 11A-11C are diagrams illustrating a single-color SrQPM system, or a multi-spectral SrQPM system, that can be implemented within a standard off-the-shelf microscope system for quantitative dispersion measurements, according to the present application;

FIGS. 12 and 12-1 include a diagram illustrating a self-referenced common-path low-coherence, wide-field reflection phase microscope to image a sample, according to the present application;

FIGS. 13A-13C are diagrams illustrating a two-step polarization-sensitive diffraction phase microscope, according to the present application; and FIGS. 14A-14C are diagrams illustrating a single-shot polarization-sensitive diffraction phase microscope according to the present application.

DETAILED DESCRIPTION OF THE INVENTION

Figure 3A:
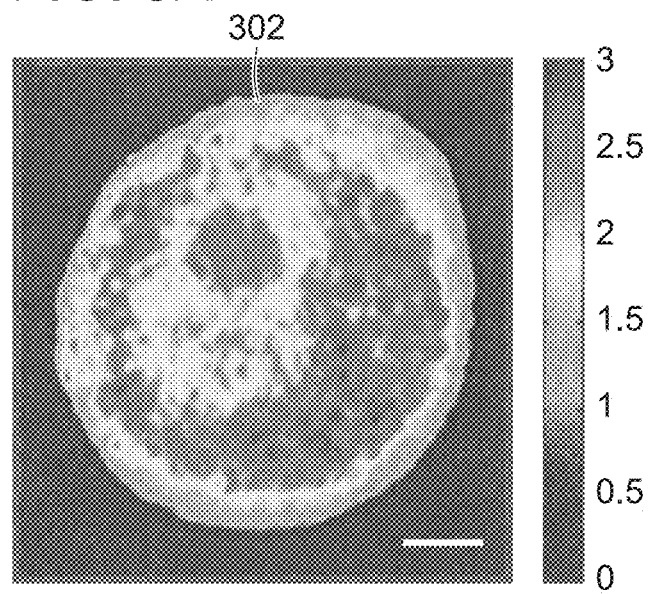
FIG. 3A illustrates a quantitative phase image of a biological sample reconstructed from an interference image.

Some embodiments described herein are directed to phase imaging systems. In one embodiment, the system includes a sampling region positioned to receive light illuminating a sample in a first portion of the sampling region and illuminating a second portion of the sampling region that does not include the sample. The system also includes a separating optical element that separates a zero-th order light component and a higher order light component from light incident on the separating optical element from the sampling region. The system also includes a first optical element that modifies the zero-th order light component and a second order optical element that modifies the higher order light component. The modified zero-th order light component and the modified higher order light components are coupled to a detector device to generate interference image data. Thus, preferred embodiments involve the separation and optical processing of different orders of light for quantitative phase imaging.

FIG. 1A depicts an illustrative embodiment of an exemplary self-referenced quantitative phase microscopy (SrQPM) system 100, in accordance with the present application. The SrQPM system 100 has single-shot, wide-field imaging capability for increased imaging speed, and nearcommon-path geometry for increased phase stability, allowing the study of internal structures of biological cells, live cell dynamics, and the like.

In the illustrated embodiment, the exemplary SrQPM system 100 (see FIG. 1A) includes a light source 102, an inverted microscope 104 including an objective lens 107, a mirror 108, and a lens 110, a plurality of magnification lenses 112, 114, a mirror 115, a separating optical element such as a diffraction grating 116, an imaging system 117, which includes lenses 118, 124 and inverting optical elements in the form of a pair of prisms 120, 122, and a detector 126. The SrQPM system 100 may further include at least one computer (see, e.g., computer 580; FIG. 5A) communicably coupled to the light source 102 and the detector 126. The computer includes at least one processor (see, e.g., processor 582; FIG. 5A) operative to execute at least one program out of at least one memory (see, e.g., memory 584; FIG. 5A) to control the operation of the light source 102 and the detector 126, and to perform data collection and analysis.

For example, the light source 102 can be a highly spatially coherent light source, such as a 637 nm fiber-coupled laser diode, or any other suitable light source. Further, the microscope 104 may be an Olympus IX71 microscope or any other suitable microscope, the objective lens 107 can be a 40×/0.65 NA objective lens or any other suitable objective lens, and the diffraction grating 116 can be a 1000 LPI diffraction grating or any other suitable diffraction grating. Other suitable devices can be used to separate the two-components of light incident from the sampling region to provide the required interference patterns at the imaging plane. In addition, the imaging system 117 may be a 4f imaging system or any other suitable imaging system, the pair of prisms 120, 122 may be a pair of dove prisms or any other suitable inverting prisms that modify the light components, and the detector 126 may be a high-speed Photron 1024PCI CMOS camera or any other suitable detector. In other embodiments, the inverting optical elements may be reflective optical elements instead of, or in addition to, refractive optical elements.

In accordance with an exemplary mode of operation, light 130 from a single-mode fiber of the light source 102 is collimated and incident upon a sampling region that has a first portion including a sample 106 and a second portion that does not include the sample. The second portion that does not include the sample may be referred to as a bypass portion or a bypass region herein. The sampling region may include part or all of the field-of-view of the objective lens. In some embodiments, the sample can occupy one-half or less of the sampling region (e.g., of the field-of-view of the objective lens 107). As shown in FIG. 1a, the light 130 is collected by the objective lens 107, reflected off of the mirror 108, and passed through the lens 110 to a first image plane $IP_1$. The light 130 is passed through the first image plane $IP_1$, magnified by the lenses 112, 114, reflected off of the mirror 115, and incident upon the diffraction grating 116 in a conjugate image plane $IP_2$. A zero-th order beam (0) and a first order beam (+1) are generated by the diffraction grating 116, and subsequently passed through the lens 118. The first order beam (+1) and the zero-th order beam (0) are also passed through the pair of prisms 120, 122, respectively, and ultimately passed through the lens 124 to be recombined and imaged onto a detection plane of the detector 126.

In the illustrative embodiment of FIG. 1A, the prisms 120, 122 are respective dove prisms oriented in different directions, preserving equality between the optical path lengths of the first and zero-th order beams (+1, 0). For example, if the overall direction of the beam paths at the prisms 120, 122 is defined to be parallel to the z-axis, both prisms 120, 122 have their longitudinal axis roughly aligned with the z-axis, but the short surfaces of the prisms 120, 122 face in different directions. If the short surface of the prism 122 is normal to the y-axis, the short surface of the prism 122 may be normal to the x-axis (see also FIG. 1B). More specifically, the dove prisms 120, 122 are oriented such that the dove prism 120 vertically flips an image 134 (see FIG. 1C) formed by the first order beam (+1) relative to an original image 132 (see FIG. 1C) of the sample 106, and the dove prism 122 horizontally flips an image 136 (see FIG. 1C) formed by the zero-th order beam (0) relative to the original image 132 of the sample 106. Having passed the different order light components, that is, the first and zero-th order beams (+1, 0) through the dove prisms 120, 122, respectively, the image 136 formed by the zero-th order beam (0) represents a 180° rotated version of the image 134 formed by the first order beam (+1) (see also FIG. 1C).

FIG. 1B is a ray-tracing diagram illustrating how the dove prism 122 can operate to horizontally flip the image 136 formed by the zero-th order beam (0) relative to the original image 132 of the sample 106. It is noted that the dove prism 122 horizontally flips the hologram image 136 formed by the zero-th order beam (0) to generate the 180° rotated version of the hologram image 134 formed by the first order beam (+1) before the respective hologram images 134, 136 are recombined and imaged onto the detection plane.

FIG. 1C depicts an exemplary representation of the original image 132 of the sample 106, an exemplary representation of the image 134 formed by the first order beam (+1) vertically flipped relative to the original image 132 of the sample 106, and an exemplary representation of the image 136 formed by the zero-th order beam (0) horizontally flipped relative to the original image 132 of the sample 106. As shown in FIG. 1C, the image 136 formed by the zeroth order beam (0) represents a 180° rotated version of the image 134 formed by the first order beam (+1). FIG. 1C further depicts a holographic interference pattern 138 formed by interference of the image 134 with the image 136 at the detection plane.

It is noted that an angular separation between the first and zero-th order beams (+1, 0) at the detection plane gives rise to a high-frequency carrier incorporated into the holographic interference pattern 138, permitting single-shot (off-axis) holography to be performed. It is further noted that the light source 102 implemented as a highly spatially coherent light source allows the first and zeroth order beams (+1, 0) to be recombined and imaged onto the detection plane after the first and zeroth order beams (+1, 0) have been vertically/horizontally flipped or rotated by the dove prisms 120, 122, respectively.

The resulting hologram image 138 (see FIG. 1C) formed from interference of the first and zero-th order beams (+1, 0) may undergo exemplary processing as follows. In the exemplary processing of the hologram image 138 described below, the detector 126 (see FIG. 1A) is implemented as a high-speed CMOS camera. Further, at the CMOS camera in (x,y)-space, two wave fields corresponding to the first and zero-th order beams (+1, 0) are denoted as "$E_{+1}(x,y)$" and "$E_0(x,y)\exp(jk_x x)$", respectively, in which "$k_x$" corresponds to the carrier frequency.

An intensity profile, $H(x,y)$, of the recorded hologram image 138 can be expressed as follows, $$H(x,y)=|E_{+1}(x,y)+E_0(x,y)\exp(jk_x x)|^2$$

$$H(x,y)=|E_{+1}|^2+|E_0|^2+E_{+1}E_0^*\exp(-jk_x x)+E_{+1}^*E_0\exp(jk_x x). \quad (1)$$

The carrier frequency, $k_x$, ensures that the terms "$E_{+1}E_0^* \exp(-jk_xx)$" and "$E_{+1}^*E_0 \exp(jk_xx)$" in equation (1) above are displaced from the origin (in opposite directions) in spatial frequency space. Accordingly, after transforming the recorded hologram images using the Fourier transform, all terms except for the term, $E_{+1}E_0^* \exp(-jk_xx)$, can be suppressed by an amplitude mask.

It is noted that the effect of the carrier frequency, $k_g$, can be reduced or removed by translating the term, $E_{+1}E_0^* \exp(-jk_xx)$, in Fourier space, to the origin. The resulting holographic reconstruction of the sample 106 can be expressed as follows, $$T(x,y)=E_{+1}(x,y)E_0^*(x,y). \quad (2)$$

If it is assumed that the sample 106 (see FIG. 1A) acts as a phase mask with a phase profile denoted as "$\phi(x, y)$", then the wave fields corresponding to the first and zero-th order beams (+1, 0) can be expressed as follows, $$E_{+1}(x, y)=\exp[j\phi(x, y)], \text{ and} \quad (3)$$

$$E_0(x, y)=\exp[j\phi(-x, -y)], \quad (4)$$

in which the origin of the (x,y) coordinate system corresponds to the intersection point between the axes of symmetry of the dove prisms 120, 122 (see FIG. 1A).

The phase profile, $\phi(x, y)$, of the sample 106 can be recovered in accordance with the following expression:

$$\text{Arg}[T(x, y)]=\phi(x, y)-\phi(-x,-y), \quad (5)$$

in which the terms "(x,y)" and "(-x,-y)" do not overlap in the image plane.

It is noted that the quality of the recovery of the phase profile, $\phi(x, y)$, performed according to equation (5) above, can be improved. For example, a hologram image recorded in the absence of the sample 106 can be used to remove systematic system-dependent phase variations over the field-of-view. Two-dimensional phase unwrapping can then be applied to the resulting corrected phase profile so that the phase profile, $\phi(x, y)$, can be interpreted as an optical height map. Further, any residual phase ramp occurring in the quality-improved recovery of the phase profile, $\phi(x, y)$, can be removed, for example, by fitting such a phase ramp to the background region of the sample plane.

Moreover, the two distinct recoveries of the phase profile, $\phi(x, y)$, can be combined to reduce the phase noise. For example, the two phase profiles, $\phi(x, y)$, can be averaged. It is noted, however, that such averaging of the phase profiles, $\phi(x, y)$, may not account for potential residual relative defocus between the respective phase profiles.

For this reason, the Fourier transforms, $E_{+1}(v_x, v_y)$ and $E_0(v_x, v_y)$, of the wave fields, $E_{+1}(x, y)$ and $E_0(x, y)$, respectively, can be defined. Further, each phase profile, $\phi(x, y)$, can be considered in spatial frequency space; for example, the phase profile, $\phi(x, y)$, may be recovered in accordance with $\text{Arg}[E_{+1}E_0^*]$. If the phase profile, $\phi(x, y)$, is found to contain a systematic linear phase ramp, then some residual displacement may exist between the two recoveries of the phase profile, $\phi(x, y)$, even after rotation is accounted for. Moreover, other polynomial phase terms may exist corresponding to different relative aberrations in the phase profile, $\phi(x, y)$. For example, a circularly symmetric quadratic phase term can correspond to defocus. By fitting a low-order polynomial to the phase profile, $\phi(x, y)$, and correcting for it, for example, by distributing its complex conjugate evenly between $E_{+1}$ and $E_0^*$, a near-perfect matching can be achieved between the recoveries of the phase profile, $\phi(x, y)$, without suppressing or eliminating any legitimate sample features that should appear in each recovery of the phase profile, $\phi(x, y)$.

It is noted that, in the SrQPM system 100 (see FIG. 1A), the total optical power delivered to the detector 126 is generally increased compared to conventional DPM systems that include a Fourier-plane pinhole spatial filter. The SrQPM system 100 can therefore provide an improved detection signal-to-noise ratio (SNR), which can help to reduce phase error in the system. The combination of the images 134, 136 at the detection plane can also result in a further reduction of the phase error by a factor of about $\sqrt{2}$. It is also noted that systematic phase errors in the background region of the sample plane, due to, for example, the imperfect optical flatness of a microscope slide, may be manifested in the recovery of the phase profile, $\phi(x, y)$. Because such systematic phase errors are static, they are generally considered to have minor significance in the measurement of sample dynamics.

The operation of the SrQPM system 100 will be further understood with reference to the following illustrative examples, as well as FIG. 1A, FIGS. 2A-2G, and FIGS. 3A-3E. In a first example, the sample 106 (see FIG. 1A-1) is a 40-μm polymer microsphere immersed in oil with refractive index of 1.55. FIG. 2A depicts a single-shot hologram image 202 recorded by the SrQPM system 100 in the presence of the sample 106 and plotted on a linear grayscale, and FIG. 2B depicts a hologram image recorded by the SrQPM system 100 in the absence of the sample 106. FIG. 2C depicts a recovery of the phase profile, $\phi(x, y)$, based on the phase difference between the first and zero-th order wave fields, following removal of the background phase ramp and two-dimensional phase unwrapping. Specifically, FIG. 2C depicts twin, phase-conjugate holographic reconstructions 204, 206 of the sample 106, namely, the 40-μm polymer microsphere.

With regard to this first example, FIG. 2D depicts a cropped phase image 208 corresponding to the phase-reconstruction of holographic interference image 206 of the sample 106, after applying low-order aberration correction and image registration to ensure matching orientations and phase parity. Similarly, FIG. 2E depicts a cropped phase image 210 corresponding to the phase-reconstruction of holographic interference image 204 of the sample 106, after applying such low-order aberration correction and image registration. For example, such low-order aberration may be corrected for up to 2nd-order polynomials in Fourier space. FIG. 2F depicts a combined, mean phase profile 212 of the sample 106, namely, the 40-μm polymer microsphere, based on the phase images 208, 210 depicted in FIGS. 2D and 2E, respectively. FIG. 2G depicts a radial phase profile (shown as a solid line) for the phase image 208 that corresponds to the phase-reconstruction of holographic interference image 206 of the sample 106, and a radial phase profile (shown as a dotted line) for the phase image 210 that corresponds to the phase-reconstruction of holographic interference image 204 of the sample 106. As shown in FIG. 2G, near-perfect matching is achieved between the radial phase profile (shown as a solid line) for the phase image 208 (corresponding to holographic interference image 206), and the radial phase profile (shown as a dotted line) for the phase image 210 (corresponding to holographic interference image 204).

In a second example, quantitative phase imaging of the sample 106 (see FIG. 1A-1), namely, live RKO human colon-cancer cells, is performed. In this second example, for preparation of the sample 106, the RKO cells are dissociated from a culture flask, and placed between #1 glass cover-slips for imaging. The bottom glass cover slip acting as a substrate for supporting the sample. Further, the lateral position of the sample 106 is adjusted such that the duplicate images of an RKO cell do not overlap in the field-of-view of the SrQPM system 100. Hologram images are recorded, both with and without the sample 106 present, and subsequently processed in a manner similar to that described above.

Figure 3B:
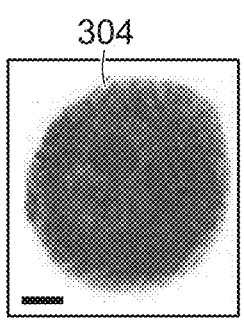
FIG. 3B illustrates a digital simulated bright-field phase-contrast image of the sample of FIG. 3A.
Figure 3C:
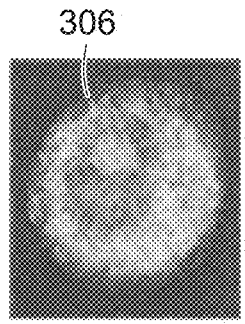
FIG. 3C illustrates a digital simulated dark-field phase-contrast image of the sample of FIG. 3A.
Figure 3D:
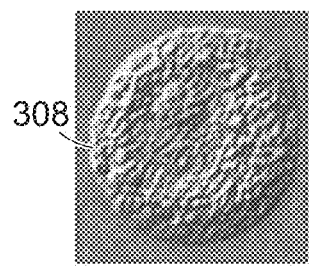
FIGS. 3D-3E illustrate variations of simulated differential interference contrast (DIC) images of the sample of FIG. 3A.
Figure 3E:
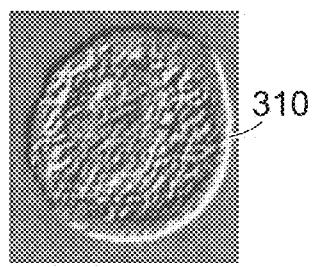

With regard to this example, FIG. 3A depicts a quantitative phase image 302 of the sample 106, namely, the RKO cell, obtained from the measured interferogram, i.e., the phase profile, $\phi(x, y)$. FIG. 3B depicts a digital simulated bright-field phase-contrast image 304 of the sample 106, according to the phase profile, $\cos [\phi(x, y)]$. FIG. 3C depicts a digital simulated dark-field phase-contrast image 306 of the sample 106, according to the phase profile, $\cos [\phi(x, y)+\pi]$. In each of the digital simulated bright-field/dark-field phase-contrast images 304, 306 depicted in FIGS. 3B and 3C, respectively, it is noted that the background phase is zero. FIGS. 3D and 3E depict variations of simulated differential interference contrast (DIC) images 308, 310, respectively, of the sample 106 (i.e., the RKO cell). The DIC images 308, 310 can be obtained by applying the partial derivative operation, with respect to displacement in a diagonal direction, to the phase profile, $\phi(x, y)$, and the phase profile, $\cos^2[\phi(x, y)]$, respectively. It is noted that structures of the RKO cell, such as the cytoplasmic-nuclear boundary and nucleolus, are clearly visible in all of the images depicted in FIGS. 3A-3E.

Figure 4:
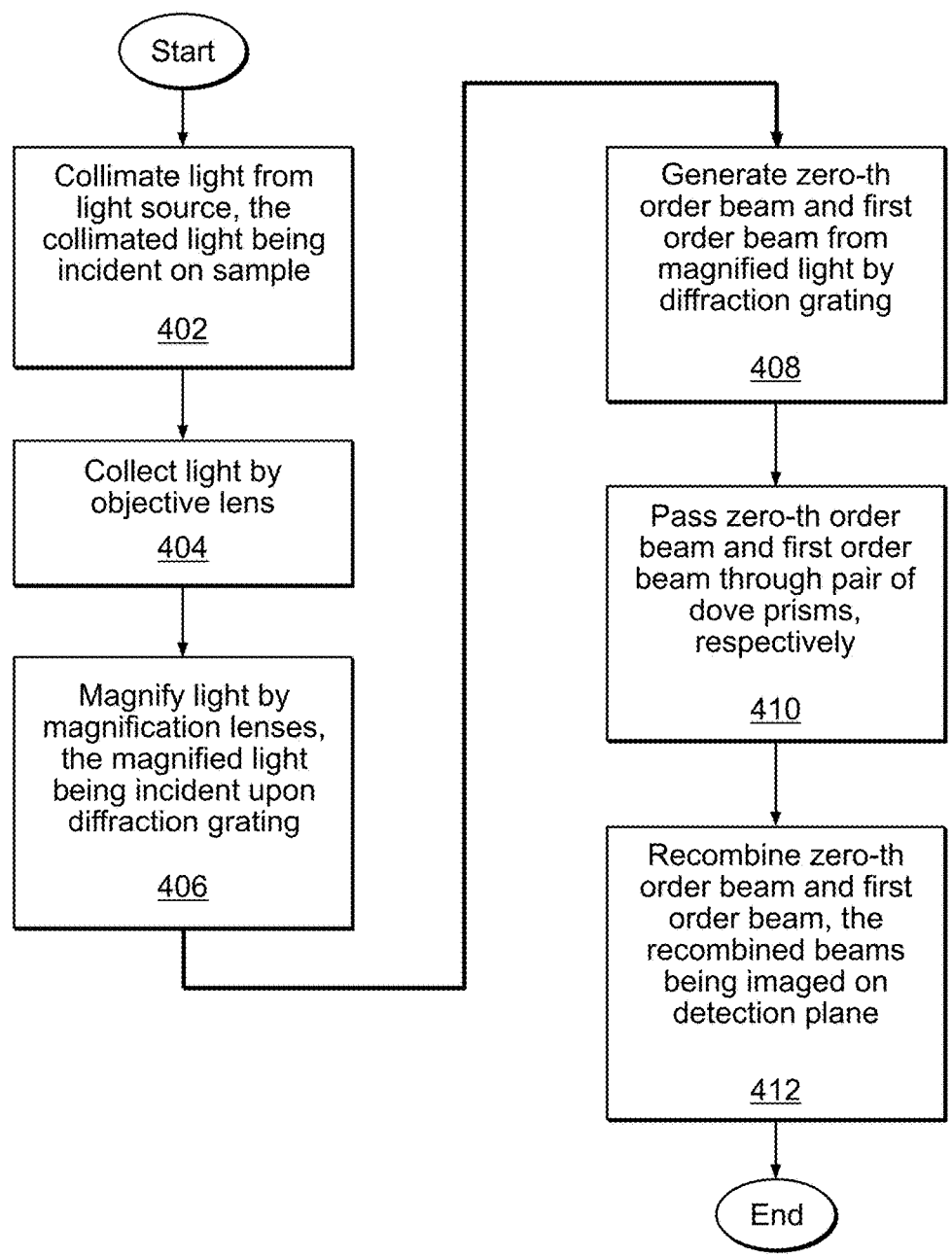
FIG. 4 is a flow diagram of an exemplary method of operating the SrQPM system of FIG. 1A.

An exemplary method of operating the SrQPM system 100 is described below with reference to FIGS. 1A and 4. As depicted in step 402 (see FIG. 4), light from the light source 102 (see FIG. 1A) is collimated and incident upon the sample 106 (see FIG. 1A-1). As depicted in step 404 (see FIG. 4), the light is collected by the objective lens 107 (see FIG. 1A). As depicted in step 406 (see FIG. 4), the light is magnified and incident upon the diffraction grating 116 (see FIG. 1A). As depicted in step 408 (see FIG. 4), a zero-th order beam (0) and a first order beam (+1) are generated from the light by the diffraction grating 116 (see FIG. 1A). As depicted in step 410 (see FIG. 4), the first order beam (+1) and the zero-th order beam (0) are passed through the pair of prisms 120, 122 (see FIG. 1A), respectively, to obtain, at the detection plane of the detector 126 (see FIG. 1A), an image formed by the zero-th order beam (0) that represents a 180° rotated version of an image formed by the first order beam (+1). As depicted in step 412 (see FIG. 4), the first order beam (+1) and the zero-th order beam (0) are recombined and imaged onto the detection plane of the detector 126 (see FIG. 1A).

Having described the above illustrative embodiments of the presently disclosed systems and methods, further alternative embodiments and/or variations may be made/practiced. For example, FIG. 5A depicts an illustrative embodiment of an exemplary multi-spectral, self-referenced quantitative phase microscopy (SrQPM) system 500, in accordance with the present application. Like the SrQPM system 100 (see FIG. 1A), the multi-spectral SrQPM system 500 (see FIG. 5A) has single-shot, full-field imaging capability for increased imaging speed, and near-common-path geometry for increased phase stability, allowing the study of internal structures of biological cells, live cell dynamics, and the like.

As shown in FIG. 5A, the multi-spectral SrQPM system 500, which includes multiple illumination sources and a near-common-path configuration, provides the capability of simultaneously acquiring wide-field multi-spectral phase information of a sample under observation. Using the multi-spectral SrQPM system 500, comprehensive and direct measurement of average RI (refractive indices) of live cells can be achieved as a function of wavelength. The multi-spectral SrQPM system 500 can be integrated into existing microscope setups for high-speed acquisition of spectroscopic phase data, which may be used to determine quantities including, but not limited to, the RI, mass, and optical dispersion parameters of the biomolecules in healthy and/or diseased cells, using a single interferogram. Because such quantities can be determined using a single interferogram, the multi-spectral SrQPM system 500 can be employed to make high-speed measurements of flowing cell samples and the like. With near real-time data processing, the multi-spectral SrQPM system 500 can characterize large numbers of cells "on-the-fly" for statistical analysis, in which comparisons between normal and abnormal cells can be made. Accordingly, the multi-spectral SrQPM system 500 may be employed in both the diagnosis and monitoring of disease processes.

As shown in FIG. 5A, the multi-spectral SrQPM system 500 includes a plurality of light sources 502, 504, 506, a plurality of beam splitters B1, B2, a lens L1, a tube lens L2, a plurality of mirrors M0, M1, M2, M3, and a detector 508. The multi-spectral SrQPM system 500 further includes at least one computer 580 communicably coupled to the light sources 502, 504, 506, the mirrors M1, M2, and the detector 508. The computer 580 includes at least one processor 582 operative to execute at least one program out of at least one memory 584 to control the operation of the light sources 502, 504, 506, the minors M1, M2, and the detector 508, and to perform data collection and analysis.

For example, the light sources 502, 504, 506 may be implemented as low-cost, compact, low voltage (e.g., 3.3 V), 405 nm (50 mW) (near-UV), 532 nm (20 mW) (green), and 780 nm (50 mW) (near-IR) diode lasers, respectively, or any other suitable light sources. FIG. 5B depicts the measured spectra for such 405 nm, 532 nm, and 780 nm diode lasers obtained using a spectrometer, illustrating that the bandwidth for each of the diode lasers is less than 2 nm. The lens L1 can be a 100× oil immersion objective lens (UPlanFLN, Olympus, Japan) or any other suitable lens, and the tube lens L2 can be an achromatic doublet lens (Newport, USA) or any other suitable lens. Further, the detector 508 may be implemented as a CCD (charge-coupled device) camera (Infinity-2, Lumenera, USA) or any other suitable detector, and the plurality of minors M0, M1, M2, M3 may be implemented as double-silver-coated minors or any other suitable mirrors.

In accordance with an exemplary mode of operation, light 512, 514, 516 from the light sources 502, 504, 506, respectively, is collimated and combined into a single beam 517 by the beam splitters B1, B2, before reaching a sample plane (SP). Having reached the sample plane SP, the single beam 517 is collected as multi-spectral light 518 by the tube lens L2. The multi-spectral light 518 is then redirected by the plurality of minors M0, M1, M2, M3 to the detector 508. Specifically, the mirror M1 (the "sample mirror M1") redirects a sample beam to the detector 508 via the minor M3, and the mirror M2 (the "reference mirror M2") redirects a reference beam to the detector 508 via the mirror M3. The field-of-view is therefore effectively divided in two, with one half of the field-of-view corresponding to the reference beam traveling through the background medium alone, and the other half of the field-of-view corresponding to the sample beam traveling through the sample plane SP. By having the sample beam and the reference beam impinge upon different mirrors, namely, the sample minor M1 and the reference minor M2, which can be tilted independently, the sample beam and the reference beam can be brought to interfere with each other at an image plane IP of the detector 508. Further, by appropriately tilting the sample and reference mirrors M1, M2, the sample beam and the reference beam can be made to travel to the image plane IP of the detector 508 substantially in parallel along a common optical path.

It is noted that, in the event the detector 508 is implemented as a color camera, its RGB channels alone may not be able to separate signals from the three diode lasers while they are simultaneously acquired at the detector 508. This may be due to the inability of a color filter array disposed at the detector 508 to achieve the desired signal separation, potentially leading to cross-talk between the respective signals. FIG. 5C depicts a diagram illustrating an exemplary RGB spectral response of the detector 508 implemented as a CCD (charge-coupled device) camera. To avoid such potential crosstalk between the diode laser signals, chromatic aberration of optical elements may be employed to provide a desired wavelength selection.

It is further noted that the achromatic doublet lens included in the tube lens L2 (see FIG. 5A), which can be designed for use in the visible region, may provide limited achromatic performance at longer and/or shorter wavelengths with respect to its center wavelength. As a result, the three laser beams (near-UV, green and near-IR) generated by the three diode lasers, respectively, may experience dissimilar "light bending" when traveling through the tube lens L2. By axially positioning the tube lens L2 so that the 532 nm (green) beam is collimated, the 780 nm (near-IR) beam becomes slightly diverging, and the 405 nm (near-UV) beam becomes slightly converging. When the reference beam and the sample beam derived from the three laser beams meet at the detector 508 (e.g., the CCD camera), interference from each diode laser can form fringes with different spacing. Variation between the different spacing of the three sets of fringes can be maximized by manipulating the angles of the sample mirror M1 and the reference mirror M2.

For example, FIGS. 6A-6F depict interferograms and corresponding fast Fourier transform (FFT) images of a 6±0.45 μm polystyrene bead (Polysciences, Inc.) in microscopy immersion oil (Type A: 1248, Cargille Labs, USA) at different wavelengths, one at a time. Specifically, FIGS. 6A-6C depict interferogram images of the polystyrene bead when each of the 780 nm, 532 nm, and 405 nm diode lasers is turned on one at a time. FIGS. 6D-6F depict the corresponding fast Fourier transform (FFT) images of the interferogram images depicted in FIGS. 6A-6C, respectively. It is noted that the spatial fringe spacing decreases from the 780 nm (near-IR) beam to the 405 nm (near-UV) beam, so that the first-order sinusoidal terms are located at different positions in spatial-frequency space. FIGS. 6G and 6H depict a single-shot three-color processing interferogram image of the same bead and its corresponding FFT image, respectively, when all three of the diode lasers are turned on at the same time.

Assuming that the sample (e.g., the polystyrene bead) under examination is transparent, a modulated intensity profile at the detector 508 (e.g., the CCD camera) can be expressed as follows, $$I_{xy}(\lambda)=\alpha(\lambda)\cos[\phi_{xy}(\lambda)+q_{xy}(\lambda)], \quad (6)$$

in which "$I_{xy}(\lambda)$" corresponds to the measured intensities, "$\phi_{xy}(\lambda)$" corresponds to the phase difference between reference and sample arms of multi-spectral SrQPM system 500, "$q_{xy}(\lambda)$" corresponds to the spatial frequency of the fringe formed by the reference and sample arms, and "$\alpha(\lambda)$" corresponds to the total intensity variation of the light source.

It is noted that the sinusoidal term in equation (6) above can be used to obtain the phase shift induced by the sample. It is further noted that the phase difference, $\phi_{xy}(\lambda)$, between the reference and sample arms can be expressed as follows, $$\phi_{xy}(\lambda)=\Delta\phi_{obj}+\phi_{bg} \quad (7)$$

in which "$\Delta\phi_{obj}$" corresponds to the relative phase delay induced by the sample with respect to the surrounding medium, and "$\phi_{bg}$" corresponds to the background phase due to mismatch between the sample beam and the reference beam.

The phase difference, $\phi_{xy}(\lambda)$, between the reference and sample arms can be recovered by using a mask to select a sinusoidal term in the Fourier domain, translating the selected region to the origin, applying the inverse FFT, and taking the argument (Arg) of the result. To fully separate contributions from the three diode laser light sources, the size of the mask can be made slightly smaller than the numerical aperture (NA) of the objective lens, cropping some of the signal. Such a constraint is not fundamental in nature, and can be resolved by using a 3-CCD camera, which utilizes a trichroic beam splitter prism to separate RGB colors to the respective CCDs.

FIGS. 6I-6K depict simultaneously acquired quantitative phase images of the same bead (e.g., the polystyrene bead) at the three diode laser wavelengths, 780 nm, 532 nm, and 405 nm, respectively, obtained from the single-shot three-color processing interferogram image depicted in FIG. 6G. As shown in FIGS. 6I-6K, the highest phase shift is observed at 405 nm, and the lowest phase shift is observed at 780 nm.

The operation of the multi-spectral SrQPM system 500 will be further understood with reference to the following illustrative example, as well as FIG. 5A, FIG. 7, and FIGS. 8A and 8B. In this example, a dispersion curve of a cell culture medium, such as the Dulbecco's Modified Eagle Medium (DMEM) or any other suitable cell culture medium, is determined through measurements of a 5±0.3 μm silica bead (Polysciences, Inc) in water and the DMEM. From a single interferogram image, the quantitative phase delay due to the silica bead in water is obtained at three wavelengths. Two sets of data are obtained and averaged. Using the known water dispersion at 20° C. and the bead size, the RI (refractive indices) of the silica bead are determined at each wavelength; exemplary measured values are 1.441±0.004, 1.427±0.002, and 1.421±0.002 at 405 nm, 532 nm, and 780 nm, respectively. Using the RI of the silica bead at the three wavelengths, the average RI of the DMEM is determined to be 1.346±0.001, 1.339±0.002, and 1.332±0.002 at 405 nm, 532 nm, and 780 nm, respectively. These three values are used to solve for the three unknowns of Cauchy's three-term formula, which is known to provide sufficient accuracy in the visible and NIR region for optical dispersion of materials, as follows, $$n(\lambda_x)=C_1+C_2\lambda_x^{-2}+C_3\lambda_x^{-4}, \quad (8)$$

in which the coefficients "$C_1$", "$C_2$", and "$C_3$" equal 1.32E0, 4.11E-3, and −1.33E-4, respectively.

Figure 7:
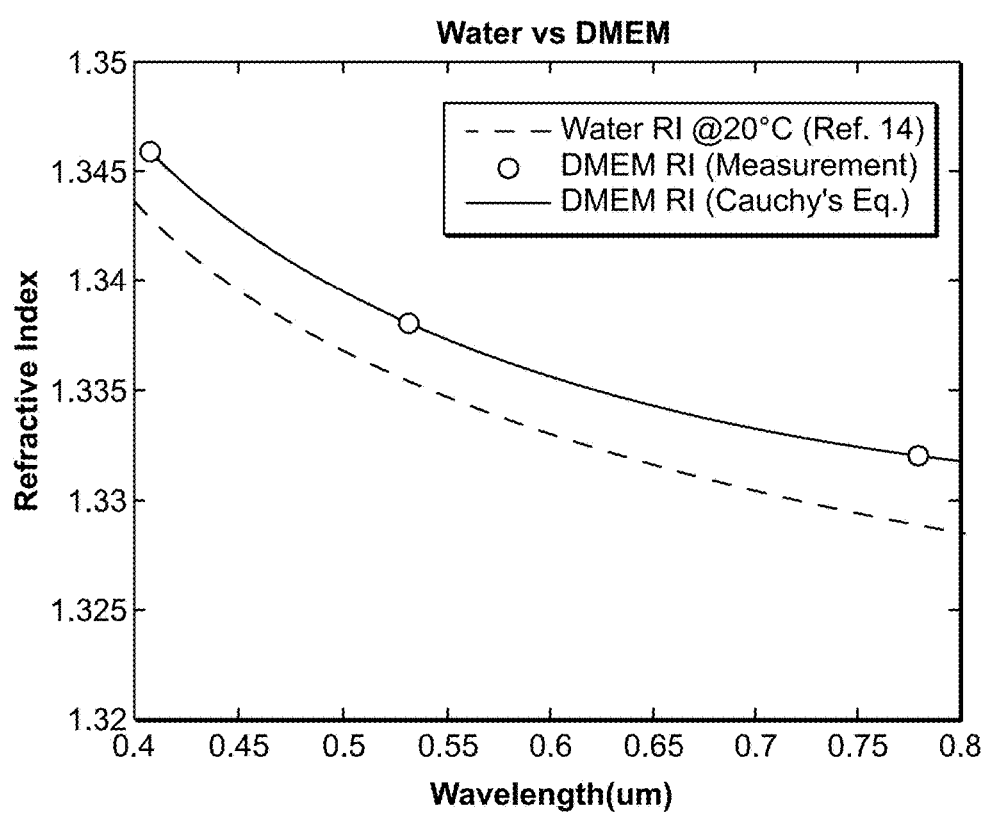
FIG. 7 is a diagram of the dispersion curve of reference water at 20° C., and the dispersion curve of a DMEM cell culture medium using an RI (refractive index) approximation derived from Cauchy's three-term formula.

FIG. 7 depicts a diagram of the dispersion curve of reference water at 20° C., and the dispersion curve of the DMEM cell culture medium using the RI approximation derived from Cauchy's three-term formula (see equation (8) above) (the three experimental values are marked with circles in FIG. 7). Because the refractive index of the DMEM is provided as a function of wavelength, its Abbe number ($v_d$) can be estimated. Further, the material's dispersion parameter based on the 486.1 nm, 587.6 nm, and 656.3 nm spectral lines can be defined as follows, $$v_d=(n_d-1)/(n_F-n_C). \quad (9)$$

In this example, the Abbe number of the DMEM is estimated to be 51.97±2.03. It is noted that the corresponding value for water at 20° C. is 55.74. Further, live cells, such as cultured RKO cancer cells, are employed as the sample. The live cells are trypsinized and resuspended with the DMEM, placed between #1 glass cover-slips using an imaging spacer with 120 μm depth (#70327-8S, EMS Inc), and transported to the multi-spectral SrQPM system 500 for imaging.

Figure 8A:
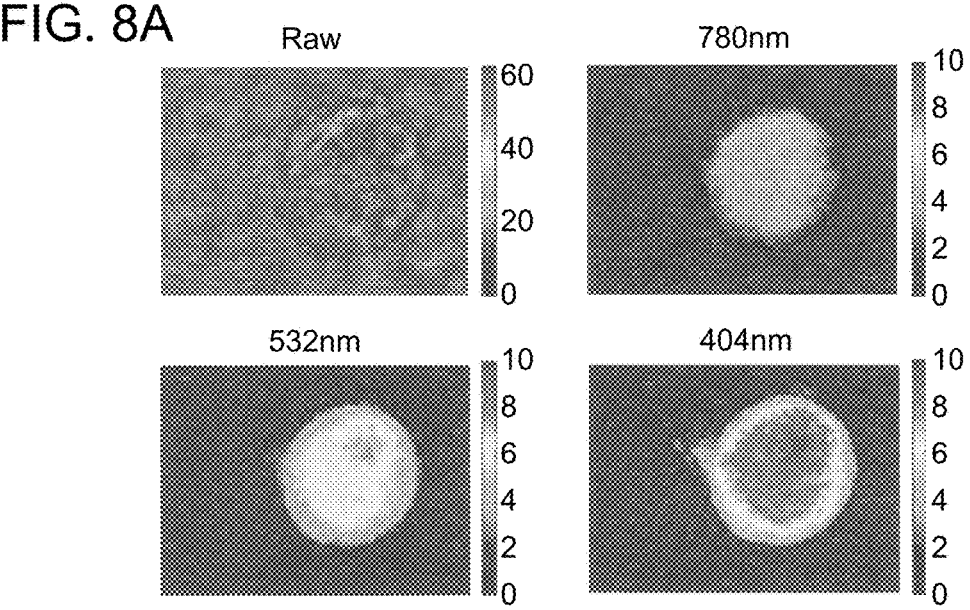
FIG. 8A illustrates a single-shot three-color interferogram image, and corresponding quantitative phase images, of an RKO human colon cancer cell at three wavelengths.
Figure 8B:
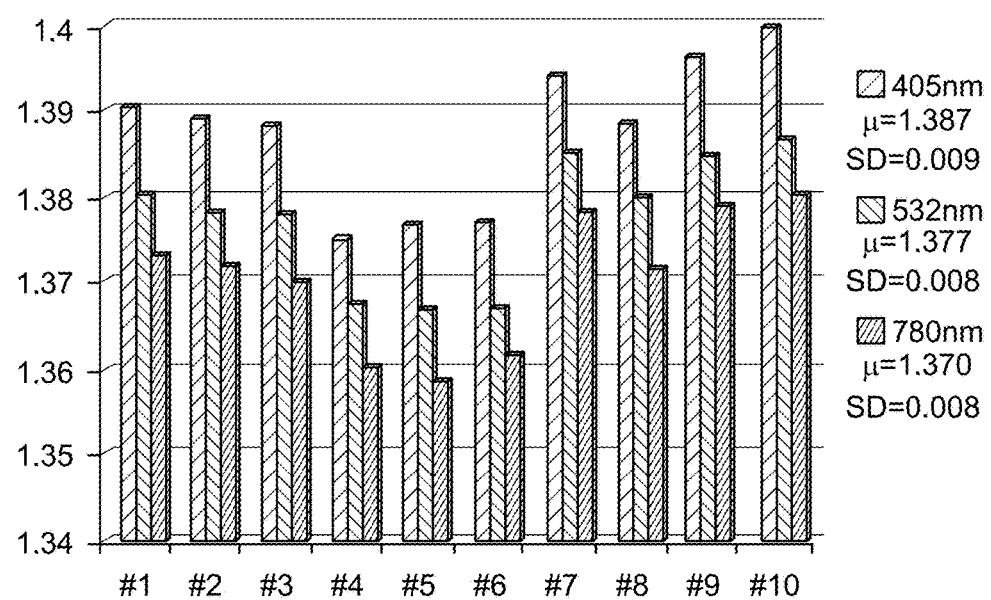
FIG. 8B is a diagram illustrating the average RIs (refractive indices) obtained from a plurality of RKO cells in suspension.

FIG. 8A depicts a single-shot three-color interferogram image (Raw), and corresponding quantitative phase images of an RKO human colon cancer cell at the three wavelengths 405 nm, 532 nm, and 780 nm.

Assuming that RKO cells in suspension have a spherical shape, the radius of each RKO cell can be obtained from its measured contour. Further, this size information for each RKO cell can be applied to decouple the average RI of the RKO cell from the measured phase. It is noted that chromatic aberrations, and imperfections in the alignment of the three laser diode light sources included in the multi-spectral SrQPM system 500, can result in different magnifications of the images at different wavelengths, requiring numerical correction prior to image co-registration. After applying such numerical correction, the average RIs (refractive indices) obtained from 10 RKO cells in suspension are found to be 1.387±0.009, 1.377±0.008, and 1.370±0.008 at 405 nm, 532 nm, and 780 nm, respectively (see FIG. 8B), using, for example, the spherical model described in Daimon M. and Masumura A., Measurement of the refractive index of distilled water from the near-infrared region to the ultraviolet region, Appl. Optics 2007, 46(18):3811-3820. Using Cauchy's three-term formula (see equation (8) above), the dispersion curve for each RKO cell can be obtained and used to determine the corresponding Abbe number. The average Abbe number of the 10 RKO cells is determined to be 51.60±4.5, which is smaller than the Abbe number of the surrounding medium due to the internal cellular protein content. It is noted that the variation of the average refractive indices among the RKO cells at a particular wavelength, which depends on the DNA contents during the cell cycle and produces considerable variation in Abbe number, can be minimized by synchronizing the cell population before the data acquisition.

Figure 8C:
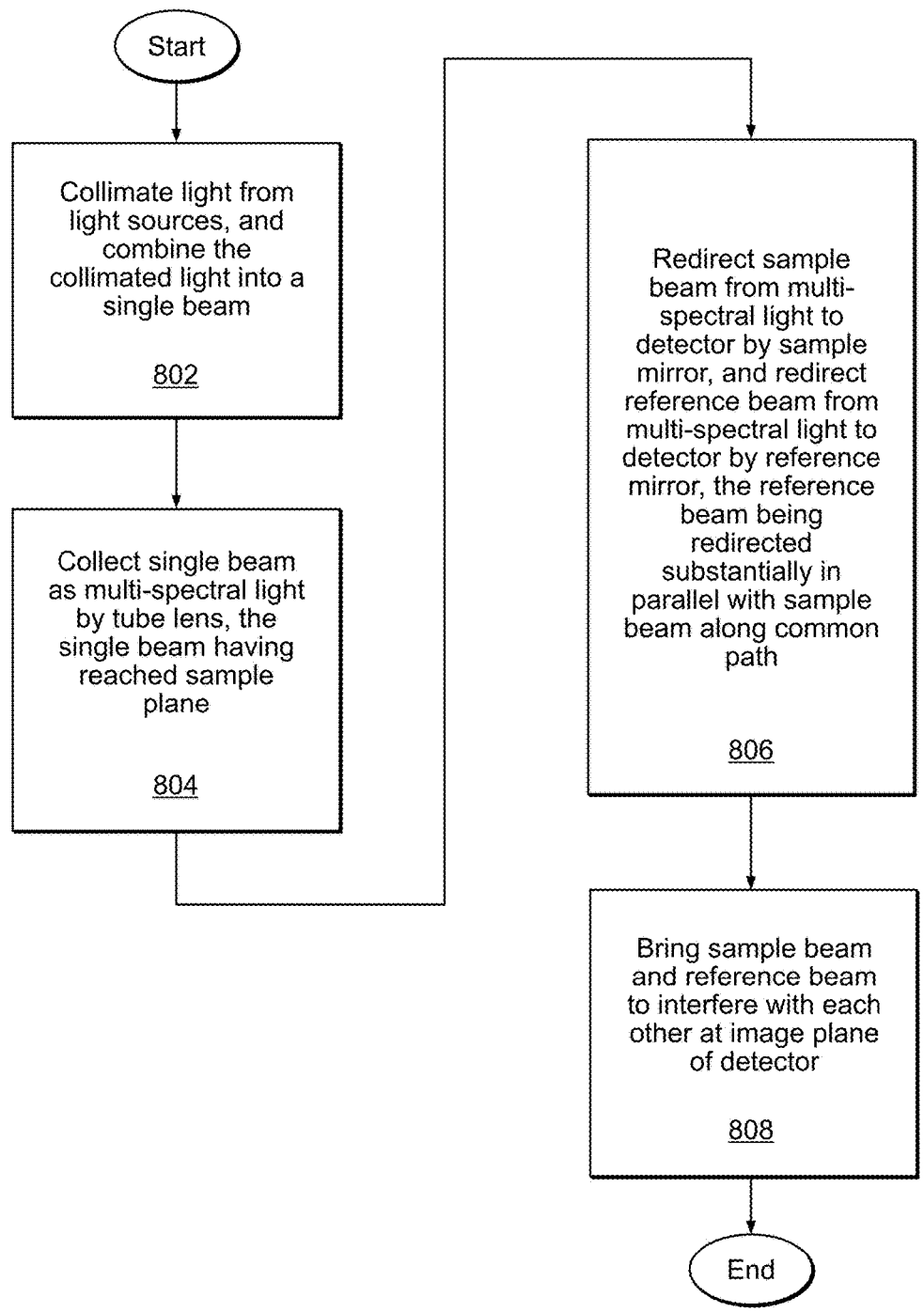
FIG. 8C is a flow diagram illustrating an exemplary method of operating the multi-spectral SrQPM system of FIG. 5A.

An exemplary method of operating the multi-spectral SrQPM system 500 is described below with reference to FIGS. 5A and 8C. As depicted in step 802 (see FIG. 8C), light from the light sources 502, 504, 506 (see FIG. 5A) is collimated and combined into a single beam by the beam splitters B1, B2, before reaching the sample plane SP. As depicted in step 804 (see FIG. 8C), having reached the sample plane SP, the single beam is collected as multi-spectral light by the tube lens L2 (see FIG. 5A). As depicted in step 806 (see FIG. 8C), a sample beam from the multi-spectral light is redirected by the sample mirror M1 (see FIG. 5A) to the detector 508 (see FIG. 5A), and a reference beam from the multi-spectral light is redirected by the reference mirror M2 (see FIG. 5A) to the detector 508 (see FIG. 5A) substantially in parallel with the sample beam along a common optical path. As depicted in step 808 (see FIG. 8C), the sample beam and the reference beam are brought to interfere with each other at an image plane IP of the detector 508 (see FIG. 5A).

FIG. 9A depicts a preferred embodiment of a multi-spectral SrQPM system 900, in accordance with the present application. As shown in FIG. 9A, the multi-spectral SrQPM system 900 includes a light source 902, an inverted microscope 904 including a mirror 908, and a lens 910, a plurality of magnification lenses 912, 914, a mirror 915, a diffraction grating 916, an imaging system 917 including lenses 918, 924 and a pair of dove prisms 920, 922, and a detector 926 such as a 2D imager. The multi-spectral SrQPM system 900 further includes at least one computer (see, e.g., computer 580; FIG. 5A) communicably coupled to the light source 902 and the detector 926. The computer includes at least one processor (see, e.g., processor 582; FIG. 5A) operative to execute at least one program out of at least one memory (see, e.g., memory 584; FIG. 5A) to control the operation of the light source 902 and the detector 926, and to perform data collection and analysis.

Because the multi-spectral SrQPM system is used without a spatial pinhole filter, a preferred embodiment of multi-spectral SrQPM system 900 (see FIG. 9A) can be implemented to accomplish single-shot, multi-spectral quantitative phase imaging. As shown in FIG. 9A, the multi-spectral SrQPM system 900 is configured to combine light from free-space or the light source 902 including a plurality of fiber-coupled laser sources 1, 2, . . . N, using a wavelength division multiplexer (WDM) device 903. The multi-spectral SrQPM system 900 can also be configured to employ a broadband source 940 (see FIG. 9B) together with a multi channel narrow band-pass filter 942 (see FIG. 9B) to generate multicolor light. Thus, this embodiment enables use of a low coherence light source.

The multi-spectral SrQPM system 900 can therefore generate collimated multi-color light for use in illuminating a sample 906. The diffraction grating 916 can be used to generate two copies of the input sample beam. Specifically, the DC light beam (the diffracted zero-th (0) order multi-wavelength beam) is rotated left-to-right (horizontally flipped) as it passes through the dove prism 922. The diffracted first (+1) order multi-wavelength beam is dispersed after the diffraction grating 916, passed through the dove prism 920 (vertically flipped), and combined with the DC beam at the detector 926. It is noted that the 4-f imaging condition between the diffraction grating 916 and the detector 926 cancels the dispersion in the diffracted beam.

It is noted that the light source 902 can include red, green, and blue diode lasers, and the detector 926 can include color filters in a color camera to separate multi-spectral interference fringes. The multi-spectral SrQPM system 900 can therefore acquire single-shot, full-field, multi-color interferograms that can be post-processed to determine wavelength-dependent optical phase delay information of the sample (see FIG. 9A-1).

Figure 10:
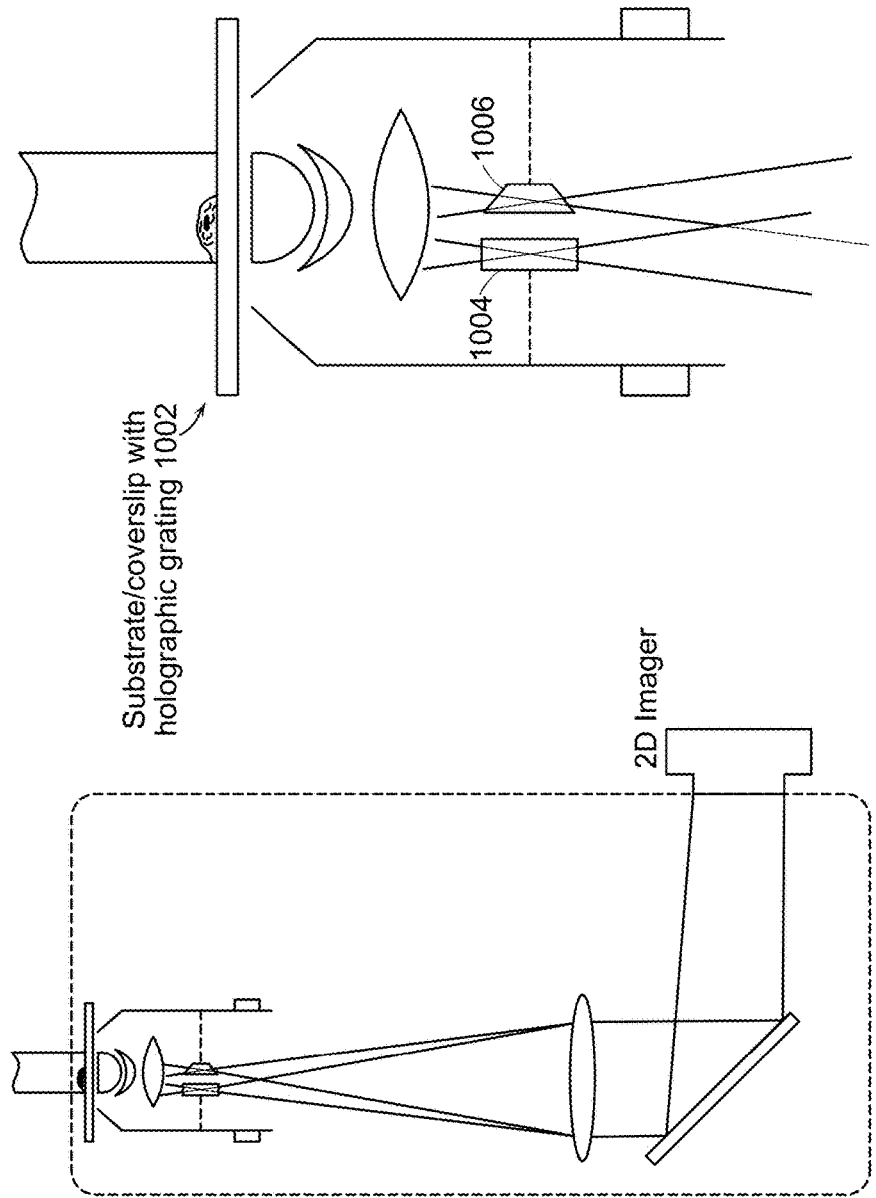
FIG. 10 is a diagram illustrating the incorporation of a diffraction grating and dove prisms within optical elements of a microscope, according to the present application.

As described above, the imaging system 117 within the SrQPM system 100 (see FIG. 1A) can include a pair of optical elements such as dove prisms 120, 122. In one alternative embodiment, the pair of dove prisms can be incorporated into the microscope 104 within the SrQPM system 100. Specifically, two features of the SrQPM system 100 include the diffraction grating 116 that generates multiple copies of the original sample beam, and the set of dove prisms 120, 122, oriented in different directions, to accomplish the interference of the sample beam with a 180° rotated version of itself. The SrQPM system 100 can be made more compact, and/or implemented within a standard off-the-shelf microscope system, by incorporating a diffraction grating and dove prisms 1004, 1006 (see FIG. 10) within the optical elements of the microscope. In one embodiment, this can be achieved by configuring a substrate for supporting a sample, for example, a glass cover-slip 1002 (for sample preparation; see FIG. 10), with a sinusoidal phase grating recorded on it. As a result, more than one copy of the sample beam (i.e., a zero-th diffraction order and one or more non-zero diffraction orders) can be generated within the microscope objective. As mentioned earlier, only two copies of the sample beam are needed for successful operation of the SrQPM system.

Furthermore, the microscope objective can be configured to hold inverting prisms, for example, the pair of small dove prisms 1004, 1006, mounted inside such that their location coincides with the back focal plane of the microscope objective. The two beams passing through the dove prisms 1004, 1006 are rotated upside-down (vertically flipped) and left-to-right (horizontally flipped), respectively, and caused to meet at the camera plane at an angle for off-axis interference. It is noted that, in this configuration, the camera can be mounted in one of the regular video ports requiring no additional modules to be built outside the microscope. In such a configuration, single-shot, off-axis interferograms can be acquired and post-processed to obtain quantitative phase information of the sample.

In another preference embodiment, a single-color SrQPM system, or a multi-spectral SrQPM system, can be implemented within a standard off-the-shelf microscope system for quantitative dispersion measurements by placing a sample 1102 (see FIG. 11B-1) in a location such that it acquires only half (e.g., the left half) of the field-of-view (see FIG. 11A). As shown in FIG. 11B, after light is passed through a tube lens 1104, the sample wave is partitioned into two halves (sample (S), reference (R)), each containing different portions of the field-of-view, using two half mirrors $M_R$, $M_s$ (see FIG. 11B). By adjusting the tilt of the mirrors $M_R$, $M_S$, the wavefront within the empty region of the field-of-view can be made to interfere with the wavefront containing the sample 1102 (see FIG. 11C). The acquired single-shot interferogram can then be post-processed to obtain quantitative phase information of the sample 1102. This embodiment uses a light source with a plurality of channels. It is noted that at least one computer (see, e.g., computer 580; FIG. 5A) is communicably coupled to a multi-channel light source (see FIG. 11B), the two half mirrors $M_R$, $M_S$, and a 2D imager (see FIG. 11B). The computer includes at least one processor (see, e.g., processor 582; FIG. 5A) operative to execute at least one program out of at least one memory (see, e.g., memory 584; FIG. 5A) to control the operation of the multi-channel light source (see FIG. 11B), the two half mirrors $M_R$, $M_S$, and the 2D imager (see FIG. 11B), and to perform data collection and analysis.

As described above, the SrQPM system 100 (see FIG. 1A) and the multi-spectral SrQPM system 500 (see FIG. 5A) each employ light transmitted through a sample to obtain quantitative phase information of the sample. In still another alternative embodiment, a self-referenced low-coherence, full-field reflection phase microscope 1204 is disclosed, as depicted in FIG. 12. As opposed to transmission phase microscopes that provide integrated phase delay through the sample (see FIG. 12-1), the low-coherence full-field reflection phase microscope 1204 offers sectioning capability via the coherence grating 1216 and thus can be used to study, for example, the dynamics of internal organelles in a complex eukaryotic cell. The reflection phase microscope 1204 also offers advantages such as high measurement sensitivity and backscattered light measurement, which is suitable for in-vivo measurements.

A known low-coherence reflection phase microscope configuration uses a diffraction grating installed in a reference arm for off-axis interference, leading to high-speed full-field quantitative phase imaging. The position of the reference mirror can be adjusted to select and measure phase profile at the depth of interest within the sample. It is noted that the separate reference arm in this known configuration may lead to phase instability. Although the phase stability can be achieved by installing a high-speed piezo actuator in the reference arm, a common-path approach is more desirable as it will automatically cancel the common-mode phase noise. The self-referenced reflection phase microscope (in FIG. 12) allows a common-path configuration to be implemented for full-field, low-coherence, reflection phase microscopy.

As shown in FIG. 12, a collimated beam from a broadband source 1202 is focused in the back focal plane of a microscope objective for full-field illumination on a sample 1206. The backscattered light carrying sample's information is imaged onto the grating 1216 in the intermediate plane (IP$_2$) using imaging optics. As in the case of multi-spectral SrQPM (shown in FIG. 9A), the DC and diffracted beams pass through dove prisms 1220, 1222, rotating upside-down (vertically flipped) and left-to-right (horizontally flipped), respectively. Further, the 4-f imaging condition between the grating 1216 and a camera 1226 (e.g., a 2D imager) cancels the dispersion in the diffracted beam. Relative optical delay between the two beams can be adjusted using optical delay elements 1260, 1262, such that the light arriving from the cover-slip surface interferes with the light from the desired depth within the sample 1206. The two beams meet each other in the detector (camera) plane at an angle for off-axis interference. The resultant single-shot interferogram can be post-processed to obtain phase information from the desired depth within the sample.

It is noted that at least one computer (see, e.g., computer 580; FIG. 5A) may be communicably coupled to the broadband light source 1202 (see FIG. 12) and the 2D imager 1226 (see FIG. 12). The computer includes at least one processor (see, e.g., processor 582; FIG. 5A) operative to execute at least one program out of at least one memory (see, e.g., memory 584; FIG. 5A) to control the operation of the broadband light source 1202 (see FIG. 12) and the 2D imager 1226 (see FIG. 12), and to perform data collection and analysis.

In yet another alternative embodiment, a polarization-sensitive diffraction phase microscope 1304 is disclosed (see FIG. 13A), in which the ability of a pair of inverting optical elements (e.g., dove prisms 1320, 1322) to generate twin sample images in a detection plane is exploited to acquire, in a single shot, the full polarization-state profile of a sample wave. The sample-wave regions corresponding to the two images are passed through different polarization analyzers, permitting simultaneous holographic acquisition of orthogonally polarized beams.

It is noted that polarization-sensitive measurements have the capability of augmenting the information content of QPM, providing anisotropy information in addition to the optical thickness profile. Such polarization-sensitive measurements permit additional structural and molecular specificity to be incorporated into biological cellular measurements. For example, FIG. 13B schematically depicts a field-of-view 1330 including a sample (see FIG. 13A-1) area 1332 and a reference area 1334 with the arrow 1331 indicating the 45° polarization of the incident light. FIG. 13B also shows an interference image 1340 including an interference image 1342 of the sample produced by the vertically polarized components of the light (polarization indicated by arrows 1343) from the first dove prism 1320 and a second interference image 1344 of the sample produced by the horizontally polarized components of the light (polarization indicated by arrows 1345) from the second dove prism 1320.

The polarization-sensitive diffraction phase microscope 1304 also permits a map of a four-element Jones matrix, the transformation between the incident and transmitted-light polarization states, to be measured in two snapshots. This is achieved by setting the polarization state of the incident light to be +45 degrees (see FIG. 13B) and −45 degrees (see FIG. 13C) for the successive exposures. The illumination and detection polarization-state pairs generate the four elements of the Jones matrix.

It is noted that at least one computer (see, e.g., computer 580; FIG. 5A) is communicably coupled to the laser (see FIG. 13A) and the 2D imager (see FIG. 13A). The computer includes at least one processor (see, e.g., processor 582; FIG. 5A) operative to execute at least one program out of at least one memory (see, e.g., memory 584; FIG. 5A) to control the operation of the laser (see FIG. 13A) and the 2D imager (see FIG. 13A), and to perform data collection and analysis.

Another preferred embodiment of a polarization-sensitive system 1400 is illustrated in FIGS. 14A-14C. In system 1400, two light sources 1406, 1408 emitting different wavelengths of light, polarized at 45° and −45° (orthogonal to each other), are coupled to an inverted microscope 1404 as described herein. In this embodiment, a color camera is used as the 2-D detector to simultaneously measure the interferograms at two different wavelengths. At the detection plane, the orthogonally oriented analyzers allow simultaneous measurement of two distinct elements of Jones matrix for each wavelength. Therefore, this system characterizes the anisotropy (in terms of Jones matrix) of the sample (see FIG. 14A-1) using different polarization components at a plurality of different wavelengths in a single step.

It is noted that at least one computer (see, e.g., computer 580; FIG. 5A) is communicably coupled to the laser @ λ1 (see FIG. 14A), the laser @ λ2 (see FIG. 14A), and the color camera (see FIG. 14A). The computer includes at least one processor (see, e.g., processor 582; FIG. 5A) operative to execute at least one program out of at least one memory (see, e.g., memory 584; FIG. 5A) to control the operation of the laser @ λ1 (see FIG. 14A), the laser @ λ2 (see FIG. 14A), and the color camera (see FIG. 14A), and to perform data collection and analysis.

System and methods of self-referenced quantitative phase microscopy (SrQPM) have been disclosed that provide a straightforward approach for generating highly sensitive phase profiles of biological samples. The disclosed systems and methods are capable of measuring temporal optical path length variations with sub-nanometer sensitivity, while avoiding the alignment issues inherent in conventional DPM, particularly during long-term imaging. The disclosed systems and methods permit the focusing objectives to be interchanged easily, without adjustment of the dove-prism pair. The disclosed systems and methods offer reduced phase noise due to the simultaneous generation of two independent representations of the sample phase profile. The reconstructed profile of a RKO human colon cancer cell, as described herein, demonstrates the capability of SrDPM to deduce the cell's intricate microscopic features. The robustness of this approach makes it suitable for modular incorporation into standard microscope systems, without introducing challenging alignment problems, rendering it more accessible to non-specialists in optics. Because the microscope design requires approximately one-half of the object field-of-view to be optically flat, it can be easily adapted to the field of microfluidic technology, in which the microchannel area is relatively small compared with the non-channelized region.

Systems and methods of multi-spectral self-referenced quantitative phase microscopy (SrQPM) have also been disclosed that can be used to study the dispersion characteristics of live cells in a single step, which does not require the sample to be stationary. The exemplary disclosed systems and methods utilize three low-cost laser diodes in the near-UV, visible, and near-IR regime. The disclosed systems and methods allow wide-field quantitative phase information of a sample under study to be obtained at the three wavelengths in a single capture. The measured phase information can be used to solve Cauchy's formula in order to obtain the optical dispersion and Abbe number of different samples, including, but not limited to, live RKO human colon cancer cells. The disclosed systems and methods can be integrated into a standard microscope for multi-spectral phase measurement of biological samples and the like.

It will be appreciated by those skilled in the art that modifications to and variations of the above-described systems and methods may be made without departing from the inventive concepts disclosed herein. Accordingly, the disclosure should not be viewed as limited except as by the scope and spirit of the appended claims.

What is claimed is:

1. A phase imaging system comprising:
   a sampling region positioned to receive light illuminating a sample in a first portion of the sampling region and illuminating a second portion of the sampling region that does not include the sample;
   a separating optical element that separates a zero-th order light component and a higher order light component from light incident on the separating optical element from the sampling region;
   a first optical element that modifies the zero-th order light component; and
   a second optical element that modifies the higher order light component, the modified zero-th order light component and the modified higher order light component being coupled to a detector device to generate interference image data.

2. The system of claim 1, wherein the separating optical element is a diffraction grating.

3. The system of claim 1, wherein the higher order light component is a first order light component.

4. The system of claim 1 further comprising an imaging optical element configured to image the zero-th order light component and the modified higher order light component at an imaging plane, wherein the first optical element and the second optical element are disposed at, or near, the imaging plane.

5. The system of claim 1, further comprising a processing device configured to calculate data representing a phase image of the sample based on the interference image data.

6. The system of claim 1, wherein the first optical element modifies the zero-th order light component relative to a first axis, and the second optical element modifies the higher order light component relative to the second axis.

7. The system of claim 1, wherein the first optical element is a first inverting optical element that inverts the zero-th order light component relative to the first axis, and the second optical element is a second inverting optical element that inverts the higher order light component relative to the second axis.

8. The system of claim 7 wherein the first inverting optical element is a first inversion prism and the second inverting optical element is a second inversion prism.

9. The system of claim 8 wherein the first inversion prism is a first dove prism and the second inversion prism is a second dove prism.

10. The system of claim 8 wherein an orientation of the first inversion prism is rotated by about 90 degrees or by about 120 degrees with respect to an orientation of the second inversion prism.

11. The system of claim 6, wherein the second axis is about perpendicular to the first axis.

12. The system of claim 1 further comprising an objective lens operative to collect light from the sampling region.

13. The system of claim 12 further comprising one or more magnification optical elements configured to magnify light collected from the sampling region.

14. The system of claim 12, wherein the sampling region is disposed on a substrate, wherein the separating element is a diffraction grating, and wherein the substrate includes the diffraction grating.

15. The system of claim 14, wherein the first optical element is a first inverting optical element that inverts the zero-th order light component relative to a first axis, and the second optical element is a second inverting optical element that inverts the higher order light component relative to a second axis.

16. The system of claim 15 wherein the first inverting optical element is a first inversion prism and the second inverting optical element is a second inversion prism.

17. The system of claim 16 wherein the first inversion prism is a first dove prism and the second inversion prism is a second dove prism.

18. The system of claim 16 wherein an orientation of the first inversion prism is rotated by about 90 degrees or by about 120 degrees with respect to an orientation of the second inversion prism.

19. The system of claim 15 wherein the objective lens is configured to hold the first inverting optical element and the second inverting optical element, the first inverting optical element and the second inverting optical element being mounted in the objective lens and positioned relative to a back focal plane of the objective lens.

20. The system of claim 1, further comprising at least one light source operative to generate light for illumination of the sampling region.

21. The system of claim 20 wherein the at least one light source is further operative to generate spatially coherent light.

22. The system of claim 10 wherein the at least one light source is further operative to generate spatially coherent, multi-spectral light.

23. The system of claim 10 wherein the at least one light source comprises a plurality of light sources collectively operative to generate multi-spectral light.

24. The system of claim 23 further including a wavelength division multiplexer (WDM) combiner operative to combine the multi-spectral light generated by the plurality of light sources.

25. The system of claim 23 further including a multi-channel narrow band-pass filter, wherein the at least one light source comprises a broadband light source, and wherein the multi-channel narrow band-pass filter is operative to filter the light generated by the broadband light source to generate multi-spectral light.

26. The system of claim 20 further comprising a beam collimator operative to collimate light from at least one light source, the collimated light being incident on the sampling region.

27. The system of claim 20 further comprising:
at least one polarizer that polarizes light for illumination of the sampling region; and
one or more polarization analyzers collectively operative to analyze a first part of the interference image with respect to a first polarization and to analyze a second part of the interference image with respect to a second polarization different from the first polarization.

28. The system of claim 27 further comprising a processing device configured to calculate data representing phase images of the sample for two different orthogonal polarizations based on the interference image data.

29. The system of claim 27, wherein the first optical element is a first inverting optical element that inverts the zero-th order light component relative to a first axis, and the second optical element is a second inverting optical element that inverts the higher order light component relative to a second axis.

30. The system of claim 27 wherein the first inverting optical element is a first inversion prism and the second inverting optical element is a second inversion prism.

31. The system of claim 30 wherein the first inversion prism is a first dove prism and the second inversion prism is a second dove prism.

32. The system of claim 30 wherein an orientation of the first inversion prism is rotated by about 90 degrees or by about 120 degrees with respect to an orientation of the second inversion prism.

33. The system of claim 27 further comprising an objective lens operative to collect light from the sampling region.

34. The system of claim 33 further comprising one or more magnification optical elements operative to magnify the light collected from the sampling region.

35. The system of claim 27 further comprising a collimator operative to collimate light from at least one light source for illumination of the sampling region.

36. The system of claim 27 further comprising at least one light source operative to generate light for illumination of the sample.

37. The system of claim 36 wherein the at least one light source is further operative to generate spatially coherent light.

38. The system of claim 36 wherein the at least one light source comprises a plurality of light sources collectively operative to generate multi-spectral light.

39. The system of claim 36 wherein the at least one light source comprises a plurality of light sources operative to generate the spatially coherent light, and wherein the at least one polarizer comprises a plurality of polarizers operative to polarize, substantially simultaneously, light from the plurality of light sources, respectively, at orthogonal polarizations.

40. The system of claim 1 further comprising an objective lens operative to collect backscattered light from the sampling region.

41. The system of claim 40 further comprising at least one optical delay element operative to adjust relative optical delay between the zero-th order light component and the higher order light component.

42. The system of claim 41, wherein the light illuminating the sample is broad band spatially coherent light.

43. The system of claim 42, wherein the system is a self-referenced, low-coherence, wide-field reflection phase microscopy system.

44. A method of performing self-referenced phase microscopy, comprising the steps of:
- illuminating a sampling region including a first portion having a sample and a second portion having a bypass region;
- separating light from the sampling region into a zero-th order light component and a higher order light component;
- modifying the zero-th order light component relative to a first axis;
- modifying the higher order light component relative to a second axis; and
- coupling the modified zero-th order light component and the modified higher order light component to a detector device thereby generating interference image data.

45. The method of claim 44, further comprising generating data representing a quantitative phase image of the sample based on data representing the interference image.

46. The method of claim 44, wherein the interference image data includes two spatially separate interference images of the sample.

47. The method of claim 44, wherein the first portion of the sampling region has area smaller than that of the bypass region.

48. The method of claim 44, further comprising collecting light from the illuminated sampling region using an objective lens.

49. The method of claim 48, further comprising magnifying the collected light from the illuminated sampling region.

50. The method of claim 48, wherein collecting light from the illuminated sampling using an objective lens comprises collecting the zero-th order light component and the higher order light component.

51. The method of claim 50, wherein the light is separated using a diffraction grating of a substrate, and wherein the substrate supports the sample.

52. The method of claim 44, wherein the modifying the zero-th order light component relative to the first axis comprises inverting the zero-th order light component relative to the first axis, and wherein modifying the higher order light component relative to the second axis comprises inverting the higher order light component relative to the second axis.

53. The method of claim 52, wherein the zero-th order light component is inverted using a first inversion prism and the higher order light component is inverted using a second inversion prism.

54. The method of claim 53, wherein the first inversion prism is a first dove prism and the second inversion prism is a second dove prism.

55. The method of claim 53 wherein an orientation of the first inversion prism is rotated by about 90 degrees or by about 120 degrees with respect to an orientation of the second inversion prism.

56. The method of claim 44, wherein the second axis is about perpendicular to the first axis.

57. The method of claim 44, further comprising generating light for illumination of the sampling region.

58. The method of claim 57 wherein generating light for illumination of the sampling region comprises generating spatially coherent light.

59. The method of claim 57, wherein generating light for illumination of the sampling region comprises generating multi-spectral light.

60. The method of claim 59, wherein the multi-spectral light is generated collectively by a plurality of light sources.

61. The method of claim 44, further comprising generating multi-spectral light for illumination of the sampling region by combining light from a plurality of light sources using a wavelength division multiplexer (WDM) combiner.

62. The method of claim 44 further comprising generating multi-spectral light for illumination of the sampling region by combining light from a plurality of light sources using a plurality of beam splitters.

63. The method of claim 44 further comprising generating multi-spectral light for illumination of the sampling region by filtering light from a broadband light source with a multi-channel narrow band-pass filter.

64. The method of claim 44, further comprising polarizing light used to illuminate the sampling region.

65. The method of claim 64, further comprising:
- analyzing a first portion of the interference image with respect to a first polarization; and
- analyzing a second portion of the interference image with respect to a second polarization different than the first polarization, wherein the first portion of the interference image includes a first interference image of the sample and wherein the second portion of the interference image includes a second interference image of the sample.

66. The method of claim 44, further comprising collimating the light used to illuminate the sampling region.

67. The method of claim 44, further comprising collecting backscattered light from the illuminated sampling region using an objective lens.

68. The method of claim 67 further comprising adjusting a relative optical delay between the zero-th order light component and the higher order light component before generating the obtaining interference image data.

69. The method of claim 68 wherein adjusting a relative optical delay between the zero-th order light component and the higher order light component selects a cross-section of the sampling region for phase imaging.

70. The method of claim 67 further comprising:
- adjusting a relative optical delay between the zero-th order light component and the higher order light component after obtaining the interference image; and
- obtaining a second interference image after adjusting the relative optical delay.

71. The method of claim 67 further comprising generating data representing a reflection phase image of the sample based on the interference image data.

72. The method of claim 67 wherein the second axis is about perpendicular to the first axis.

73. The method of claim 67, further comprising magnifying the backscattered light.

* * * * *